US012472369B2

(12) United States Patent
Formosa et al.

(10) Patent No.: US 12,472,369 B2
(45) Date of Patent: Nov. 18, 2025

(54) IMPLANTABLE MEDICAL LEAD SHIELD

(71) Applicant: Medtronic, Inc., Minneapolis, MN (US)

(72) Inventors: Elizabeth K. Formosa, Santa Clara, CA (US); Kevin R. Seifert, Forest Lake, MN (US); Vladimir P. Nikolski, Blaine, MN (US); Mark T. Marshall, Cape Coral, FL (US)

(73) Assignee: Medtronic, Inc., Minneapolis, MN (US)

( * ) Notice: Subject to any disclaimer, the term of this patent is extended or adjusted under 35 U.S.C. 154(b) by 311 days.

(21) Appl. No.: 18/065,861

(22) Filed: Dec. 14, 2022

(65) Prior Publication Data

US 2023/0191142 A1 Jun. 22, 2023

Related U.S. Application Data

(60) Provisional application No. 63/265,762, filed on Dec. 20, 2021.

(51) Int. Cl.

*A61N 1/39* (2006.01)
*A61N 1/05* (2006.01)
*A61N 1/362* (2006.01)

(52) U.S. Cl.

CPC ......... *A61N 1/3931* (2013.01); *A61N 1/0587* (2013.01); *A61N 1/3621* (2013.01); *A61N 1/39622* (2017.08)

(58) Field of Classification Search

None

See application file for complete search history.

(56) References Cited

U.S. PATENT DOCUMENTS

| | | | | |
|---|---|---|---|---|
| 5,327,909 | A | 7/1994 | Kiser et al. | |
| 6,699,259 | B2 | 3/2004 | Fogarty et al. | |
| 7,765,015 | B2 | 7/2010 | Johnson et al. | |
| 9,604,053 | B2 | 3/2017 | Kaplan et al. | |
| 2007/0073218 | A1 | 3/2007 | Lau et al. | |
| 2012/0029335 | A1 * | 2/2012 | Sudam | A61N 1/05 600/374 |
| 2014/0194965 | A1 | 7/2014 | Osypka | |

(Continued)

OTHER PUBLICATIONS

International Search Report and Written Opinion of International Application No. PCT/IB2022/062303 dated Mar. 3, 2023, 11 pp.

*Primary Examiner* — Mallika D Fairchild

(74) *Attorney, Agent, or Firm* — Shumaker & Sieffert, P.A.

(57) ABSTRACT

An example medical device system includes an implantable medical lead including a first defibrillation electrode and a second defibrillation electrode, the first and second defibrillation electrodes configured to deliver antitachyarrhythmia shocks, and a pace electrode disposed between the first defibrillation electrode and the second defibrillation electrode, the pace electrode configured to deliver a pacing pulse that generates an electric field proximate to the pace electrode. The medical device system includes a shield configured to be implanted in a patient separately from the implantable medical lead and disposed anterior at least one of the electrodes, wherein the shield is configured to impede an electric field of the electrical therapy in a direction from at least one of the first defibrillation electrode, the second defibrillation electrode, or the pace electrode away from a heart of the patient.

19 Claims, 12 Drawing Sheets

(56) References Cited

U.S. PATENT DOCUMENTS

| | | | | |
|---|---|---|---|---|
| 2014/0257444 | A1* | 9/2014 | Cole | A61B 90/39 607/116 |
| 2015/0374991 | A1 | 12/2015 | Morris et al. | |
| 2016/0022984 | A1* | 1/2016 | Oster | A61N 1/3718 607/116 |
| 2016/0158567 | A1* | 6/2016 | Marshall | A61N 1/0504 607/116 |
| 2017/0354365 | A1 | 12/2017 | Zhou | |
| 2018/0133458 | A1* | 5/2018 | Foster | A61N 1/3956 |
| 2019/0117972 | A1* | 4/2019 | Schmidt | A61B 18/14 |
| 2019/0186702 | A1 | 6/2019 | Masson | |
| 2021/0268297 | A1 | 9/2021 | Nikolski et al. | |

* cited by examiner

IMPLANTABLE MEDICAL LEAD SHIELD

This application claims the benefit of U.S. Provisional Application Ser. No. 63/265,762, filed Dec. 20, 2021, which is entitled "IMPLANTABLE MEDICAL LEAD SHIELD" and is incorporated by reference herein in its entirety.

TECHNICAL FIELD

The present application relates to implantable medical leads and, more particularly, implantable medical leads with one or more structures to reduce the likelihood of stimulation of unintended tissue.

BACKGROUND

Malignant tachyarrhythmia, for example, ventricular fibrillation (VF), is an uncoordinated contraction of the cardiac muscle of the ventricles in the heart, and is the most commonly identified arrhythmia in cardiac arrest patients. If this arrhythmia continues for more than a few seconds, it may result in cardiogenic shock and cessation of effective blood circulation. As a consequence, sudden cardiac death (SCD) may result in a matter of minutes.

In patients with a high risk of VF, the use of implantable systems, such as an implantable cardioverter defibrillator (ICD) system, has been shown to be beneficial at preventing SCD. Implantable systems, such as pacemakers with or without cardioversion or defibrillation capabilities, may also treat other cardiac dysfunction, such as bradycardia and heart failure. Such implantable systems may include electrical devices configured to deliver therapy via electrodes. Therapy may include shocks and/or anti-tachycardia pacing (ATP). The implantable systems may also be configured to deliver cardiac pacing to, for example, treat bradyarrhythmia or for cardiac resynchronization therapy (CRT).

An implantable system may include one or more implantable medical leads. A distal portion of an implantable medical lead may include one or more electrodes, and may be positioned at a target location within the patient for delivery of electrical therapy and/or electrical sensing via the electrodes. A proximal end of the lead may be coupled to the implantable system. The implantable system may also include one or more housing electrodes, which are sometimes referred to as can electrodes, for delivery of therapy and/or sensing.

Owing to the inherent surgical risks in attaching and replacing implantable medical leads directly within or on the heart, subcutaneous implantable systems have been devised, in which the implantable system and leads are located subcutaneously outside of the thorax. It has also been proposed that the distal portion of a lead of an implantable system may be implanted within the thorax, but not in contact with the heart, e.g., substernally. Additionally, it has been proposed to implant the distal portion of a lead of an implantable system within an extracardiac vessel that is within the thorax, such as the internal thoracic vein (ITV), the intercostal veins, the superior epigastric vein, or the azygos, hemiazygos, and accessory hemiazygos veins.

Implantable medical leads are also used to deliver therapies to tissues other than the heart. Implantable medical leads may be used to position one or more electrodes within or near target nerves, muscles, or organs to deliver electrical stimulation to such tissues. As examples, implantable medical leads may be positioned in the epidural space to deliver spinal cord stimulation, or proximate to other nerves, such as pelvic nerves or renal nerves, to deliver neuro stimulation to the nerves.

SUMMARY

Relative to electrodes on or within the heart, delivery of pacing pulses or defibrillation using electrodes of extravascular or other extracardiac leads may require higher energy levels to capture and/or defibrillate the heart. Furthermore, conventional pace electrodes placed extravascularly may direct a significant portion of the electrical field produced by a pacing pulse away from the heart. The electrical field directed away from the heart may stimulate extracardiac tissue, such as the phrenic nerve, nerve endings in the intercostal regions, or other sensory or motor nerves. These issues may similarly occur when electrodes are implanted within extracardiac vessels within the thorax, such as the ITV, the intercostal veins, the superior epigastric vein, or the azygos, hemiazygos, and accessory hemiazygos veins, or when electrodes are implanted in other extracardiac locations.

The placement of extravascular ICD leads within patients having prior sternotomies is not well known. When a patient undergoes a sternotomy, which is performed in cases of open-heart surgery, coronary artery bypass grafting, and other thoracic procedures, adhesions can form between the heart and the sternum as the body heals. These adhesions, which increase the risks associated with subsequent thoracic procedures, may make it difficult to place extravascular ICD leads in the substernal space, and additionally the pacing therapy may be perceived by the patient.

This disclosure describes implantable medical leads and implantable systems, such as ICD systems, utilizing the leads. More particularly, this disclosure describes systems including implantable medical leads and separately implantable shields configured to impede the electric field from the implantable medical lead, e.g., block or reduce the electric field, in a direction from the implantable medical lead and the heart, e.g., an anterior direction. In this manner, relative to fixed shields, the shield may include more feature options and flexibility based on patient needs, e.g., flexible positioning of the shield, enabling implantation of the shield to occur at a different time than implantation of the medical device lead, easing and simplifying the process of implanting the implantable medical lead and/or the shield, increased or reduced shield sizing enabled by separate implantation to reduce the likelihood that pacing pulses delivered via the pace electrode stimulate extracardiac tissue, such as sensory or motor nerves, which may reduce pain or other sensations associated with capture of such tissue. Additionally, a separately implantable shield may reduce and/or eliminate the perception of pacing therapy by the patient and deploys easily and with proper orientation within challenging anatomy (including the adhesions described above). Furthermore, the shield may direct the electrical field toward the heart, allowing lower energy level electrical fields to capture the heart than may be required without the shield. Lower energy pacing pulses may also reduce the likelihood that pacing pulses delivered via the pace electrode stimulate extracardiac tissue, and may result is less consumption of the power source of the ICD and, consequently, longer service life for the ICD.

Although described herein primarily in the context of ICD systems, various aspects of the techniques of this disclosure may be applied to implantable systems other than ICD systems, including, but not limited to, bradycardia or CRT pacemaker systems. Accordingly, implantable medical leads having one or more shields may be used in contexts other than that of ICD systems, both cardiac and non-cardiac. As one example, implantable medical leads that have a shield over a portion of a surface of an electrode may be used with an extracardiac pacemaker system without defibrillation capabilities. As another example, implantable medical leads that have a shield over a portion of a surface of an electrode may impede an electrical field resulting from delivery of neurostimulation from the electrode in a direction away from a target nerve. In this manner, the shield may direct the neurostimulation to intended tissue, and reduce the likelihood that the neurostimulation stimulates unintended tissues.

In one example, this disclosure describes a medical device system including: an implantable medical lead including: a first defibrillation electrode and a second defibrillation electrode, the first and second defibrillation electrodes configured to deliver antitachyarrhythmia shocks; and a pace electrode disposed between the first defibrillation electrode and the second defibrillation electrode, the pace electrode configured to deliver a pacing pulse that generates an electric field proximate to the pace electrode; and a shield configured to be implanted in a patient separately from the implantable medical lead and disposed anterior at least one of the electrodes, wherein the shield is configured to impede an electric field of the electrical therapy in a direction from at least one of the first defibrillation electrode, the second defibrillation electrode, or the pace electrode away from a heart of the patient.

In another example, this disclosure describes a method including positioning an implantable medical lead at an implant location within a patient, wherein the implantable medical lead comprises: a first defibrillation electrode and a second defibrillation electrode, the first and second defibrillation electrodes configured to deliver antitachyarrhythmia shocks; a pace electrode disposed between the first defibrillation electrode and the second defibrillation electrode, the pace electrode configured to deliver a pacing pulse that generates an electric field proximate to the pace electrode; coupling a distal end of a tool to a coupling member of a shield, wherein the shield is configured to impede an electric field of the electrical therapy in a direction from at least one of the first defibrillation electrode, the second defibrillation electrode, or the pace electrode away from a heart of the patient; positioning, via the tool, the shield at the implant location; and deploying the shield between the implantable medical lead and tissue at the implant location anterior at least one of the first defibrillation electrode, the second defibrillation electrode, or the pace electrode, wherein, when deployed, the shield is configured to impede an electric field in a direction from the at least one electrode away from the heart.

In another example, this disclosure describes a shield including a biocompatible material configured to be configured to be implanted in a patient separately from an implantable medical lead and disposed anterior at least one electrode of the implantable medical lead, wherein the shield is configured to impede an electric field of the at least one electrode in a direction from the at least one electrode away from a heart of the patient; and one or more radiopaque markers configured to indicate at least one of an orientation or a position of the shield.

The details of one or more examples are set forth in the accompanying drawings and the description below. Other features, objects, and advantages will be apparent from the description, drawings, and claims.

This summary is intended to provide an overview of the subject matter described in this disclosure. It is not intended to provide an exclusive or exhaustive explanation of the systems, devices, and methods described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

As used herein, relational terms, such as "first" and "second," "over" and "under," "front" and "rear," and the like, may be used solely to distinguish one entity or element from another entity or element without necessarily requiring or implying any physical or logical relationship or order between such entities or elements.

Figure 1A:
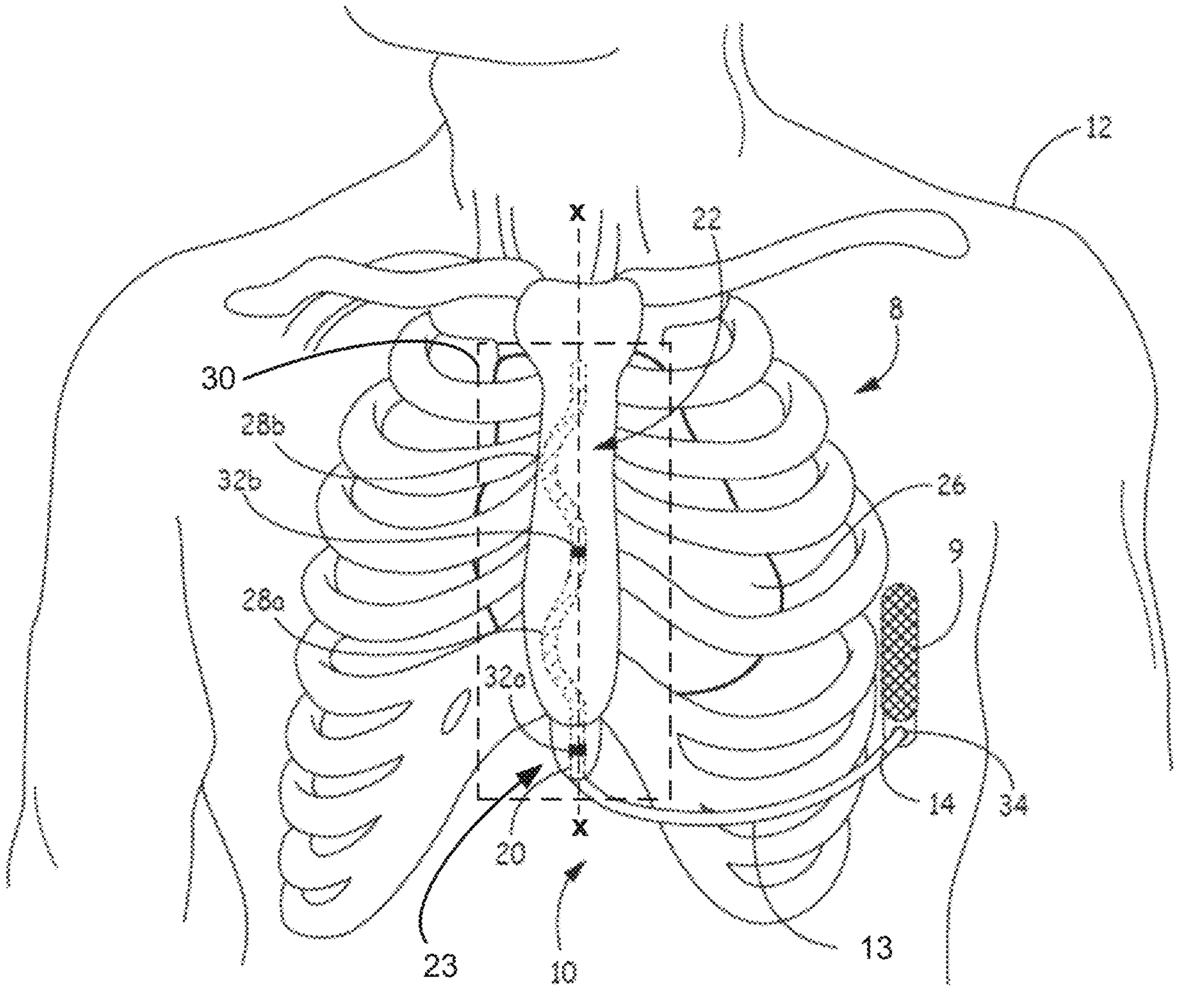
FIG. 1A is a front view of a patient with an extracardiovascular ICD system including a lead implanted intra-thoracically.
Figure 1B:
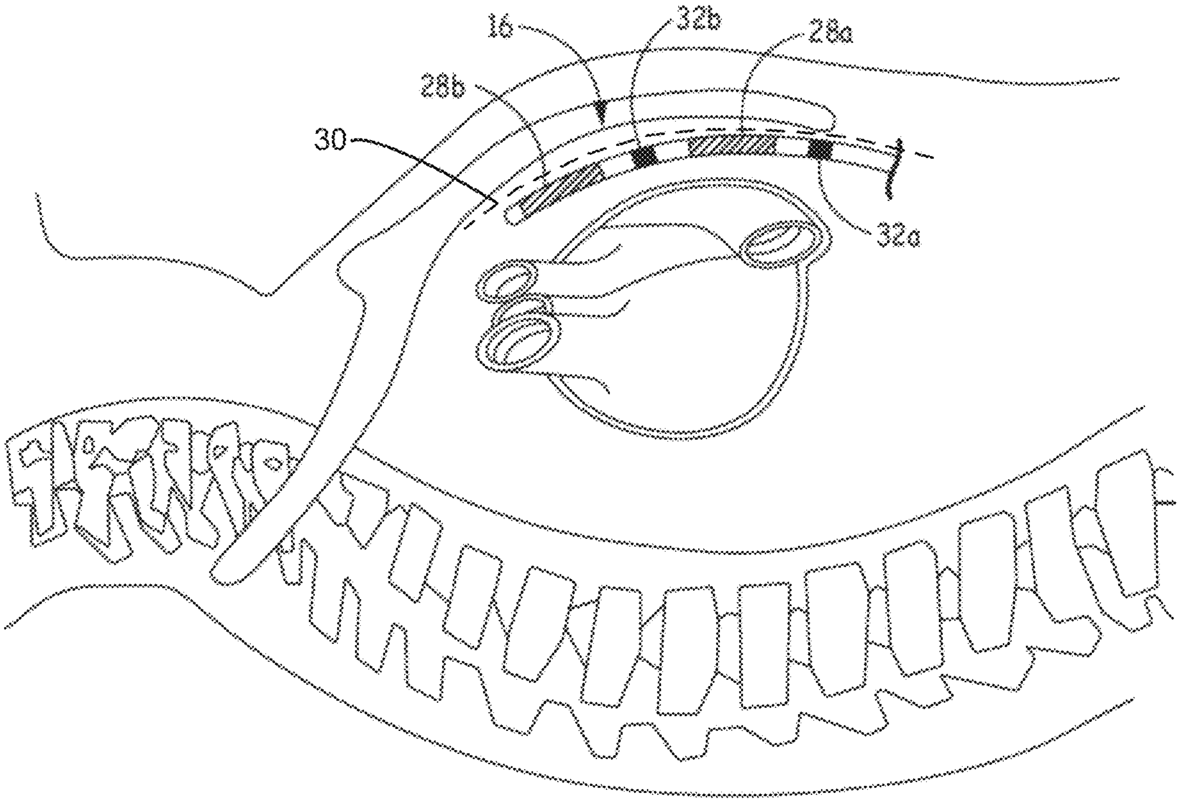
FIG. 1B is a side view of the patient with the extracardiovascular ICD system having the lead implanted intra-thoracically.
Figure 1C:
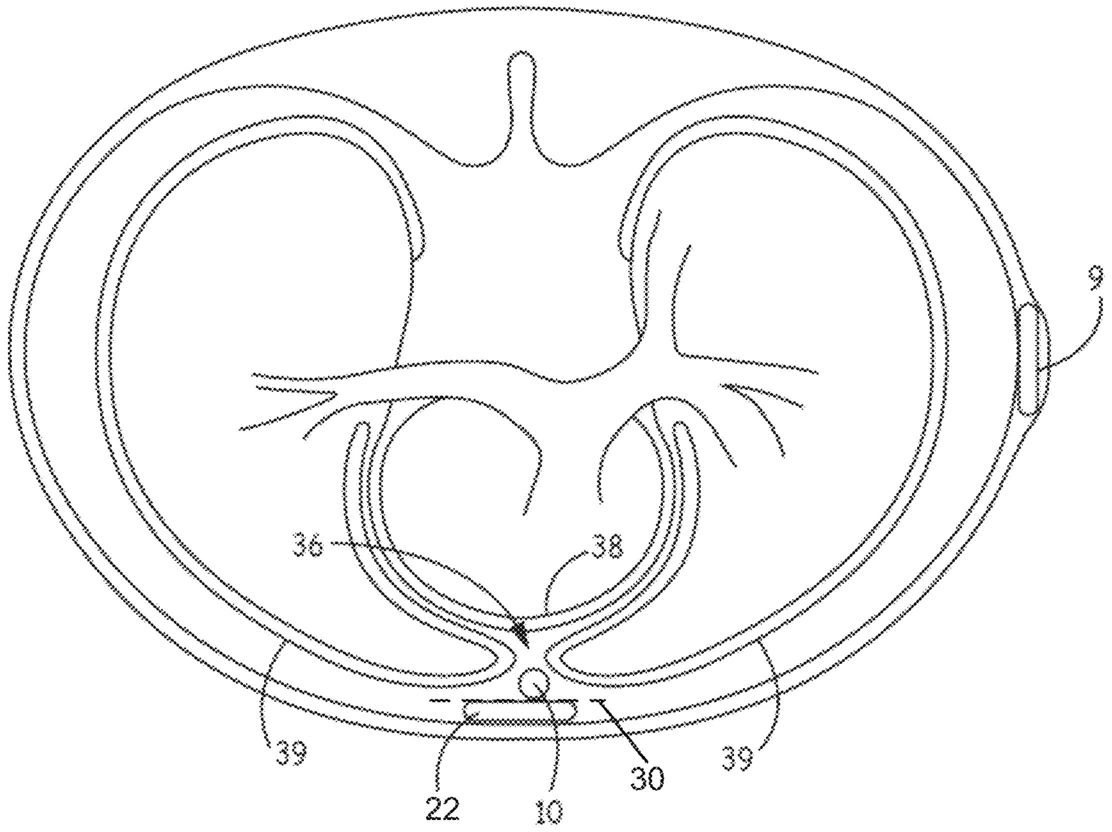
FIG. 1C is a transverse view of the patient with the extracardiovascular ICD system having the lead implanted intra-thoracically.

Referring now to the drawings in which like reference designators refer to like elements, there is shown in FIGS. 1A-C conceptual diagrams illustrating various views of an example extracardiovascular implantable cardioverter-defibrillator (ICD) system 8. ICD system 8 includes an ICD 9 connected to an implantable medical lead 10 and a separately implantable shield 30. FIG. 1A is a front view of a patient 12 implanted with extracardiovascular ICD system 8. FIG. 1B is a side view of the patient 12 implanted with extracardiovascular ICD system 8. FIG. 1C is a transverse view of the patient 12 implanted with extracardiovascular ICD system 8.

ICD 9 may include a housing that forms a hermetic seal that protects components of the ICD 9. The housing of ICD 9 may be formed of a conductive material, such as titanium or titanium alloy, which may function as a housing electrode (sometimes referred to as a can electrode). In some embodiments, ICD 9 may be formed to have or may include a plurality of electrodes on the housing. ICD 9 may also include a connector assembly (also referred to as a connector block or header) that includes electrical feedthroughs through which electrical connections are made between conductors of lead 10 and electronic components included within the housing of ICD 9. As will be described in further detail herein, the housing may house one or more processors, memories, transmitters, receivers, sensors, sensing circuitry, therapy circuitry, power sources and other appropriate components. The housing is configured to be implanted in a patient, such patient 12.

ICD 9 is implanted extra-thoracically on the left side of the patient, e.g., under the skin and outside the ribcage (subcutaneously or submuscularly). ICD 9 may, in some instances, be implanted between the left posterior axillary line and the left anterior axillary line of the patient. ICD 9 may, however, be implanted at other extra-thoracic locations on the patient as described later.

Lead 10 may include an elongated lead body 13 having a distal portion 16 sized to be implanted in an extracardiovascular location proximate the heart, e.g., intra-thoracically, as illustrated in FIGS. 1A-C, or extra-thoracically. For example, lead 10 may extend extra-thoracically under the skin and outside the ribcage (e.g., subcutaneously or submuscularly) from ICD 9 toward the center of the torso of the patient, for example, toward the xiphoid process 23 of the patient. At a position proximate xiphoid process 23, the lead body 13 may bend or otherwise turn and extend superiorly. The bend may be pre-formed and/or lead body 13 may be flexible to facilitate bending. In the example illustrated in FIGS. 1A-C, the lead body 13 extends superiorly intra-thoracically underneath the sternum, in a direction substantially parallel to the sternum.

In one example, distal portion 16 of lead 10 may reside in a substernal location such that distal portion 16 of lead 10 extends superior along the posterior side of the sternum substantially within the anterior mediastinum 36. Anterior mediastinum 36 may be viewed as being bounded laterally by pleurae 39, posteriorly by pericardium 38, and anteriorly by the sternum 22. In some instances, the anterior wall of anterior mediastinum 36 may also be formed by the transversus thoracis and one or more costal cartilages. Anterior mediastinum 36 includes a quantity of loose connective tissue (such as areolar tissue), adipose tissue, some lymph vessels, lymph glands, substernal musculature (e.g., transverse thoracic muscle), the thymus gland, branches of the internal thoracic artery, and the ITV.

In another example, lead body 13 may extend superiorly extra-thoracically (instead of intra-thoracically), e.g., either subcutaneously or submuscularly above the ribcage/sternum. Lead 10 may be implanted at other locations, such as over the sternum, offset to the right of the sternum, angled lateral from the proximal or distal end of the sternum, or the like. In other examples, lead 10 may be implanted within an extracardiac vessel within the thorax, such as the ITV, the intercostal veins, the superior epigastric vein, or the azygos, hemiazygos, and accessory hemiazygos veins. In some examples, distal portion 16 of lead 10 may be oriented differently than is illustrated in FIGS. 1A-1C, such as orthogonal or otherwise transverse to sternum 22 and/or inferior to heart 26. In such examples, distal portion 16 of lead 10 may be at least partially within anterior mediastinum 36.

Lead body 13 may have a generally tubular or cylindrical shape and may define a diameter of approximately 3-9 French (Fr). However, lead bodies of less than 3 Fr and more than 9 Fr may also be utilized. In another configuration, lead body 13 may have a flat, ribbon, or paddle shape with solid, woven filament, or metal mesh structure, along at least a portion of the length of the lead body 13. In such an example, the width across lead body 13 may be between 1-3.5 mm. Other lead body designs may be used without departing from the scope of this application.

Lead body 13 may be formed from a non-conductive material, including silicone, polyurethane, fluoropolymers, mixtures thereof, and other appropriate materials, and shaped to form one or more lumens (not shown), however, the techniques are not limited to such constructions. Distal portion 16 may be fabricated to be biased in a desired configuration, or alternatively, may be manipulated by the user into the desired configuration. For example, the distal portion 16 may be composed of a malleable material such that the user can manipulate the distal portion into a desired configuration where it remains until manipulated to a different configuration.

Lead body 13 may include a proximal end 14 and a distal portion 16 which include electrodes configured to deliver electrical energy to the heart or sense electrical signals of the heart. Distal portion 16 may be anchored to a desired position within the patient, for example, substernally or subcutaneously by, for example, suturing distal portion 16 to the patient's musculature, tissue, or bone at the xiphoid process entry site. In some examples, distal portion 16 may be anchored to the patient or through the use of rigid tines, prongs, barbs, clips, screws, and/or other projecting elements or flanges, disks, pliant tines, flaps, porous structures such as a mesh-like elements and metallic or non-metallic scaffolds that facilitate tissue growth for engagement, bio-adhesive surfaces, and/or any other non-piercing elements.

Lead body 13 may define a substantially linear portion 20 (FIG. 1A) as it curves or bends near the xiphoid process 23 and extends superiorly. As shown in FIG. 1A, at least a part of distal portion 16 may define an undulating configuration distal to the substantially linear portion 20. In particular, distal portion 16 may define an undulating pattern, e.g., zig-zag, meandering, sinusoidal, serpentine, or other pattern, as it extends toward the distal end of lead 10. In other configurations, lead body 13 may not have a substantially linear portion 20 as it extends superiorly, but instead the undulating configuration may begin immediately after the bend.

Distal portion 16 includes one or more defibrillation electrodes configured to deliver an anti-tachyarrhythmia, e.g., cardioversion/defibrillation, shock to heart 26 of patient 12. In some examples, distal portion 16 includes a plurality of defibrillation electrodes spaced a distance apart from each other along the length of distal portion 16. In the example illustrated by FIGS. 1A-1C, distal portion 16 includes two defibrillation electrodes 28*a* and 28*b* (collectively, "defibrillation electrodes 28").

Defibrillation electrodes 28 may be disposed around or within the lead body 13 of the distal portion 16, or alternatively, may be embedded within the wall of the lead body 13. In one configuration, defibrillation electrodes 28 may be coil electrodes formed by a conductor. The conductor may be formed of one or more conductive polymers, ceramics, metal-polymer composites, semiconductors, metals or metal alloys, including but not limited to, one of a combination of the platinum, tantalum, titanium, niobium, zirconium, ruthenium, indium, gold, palladium, iron, zinc, silver, nickel, aluminum, molybdenum, stainless steel, MP35N, carbon, copper, polyaniline, polypyrrole and other polymers. In another configuration, each of defibrillation electrodes 28 may be a flat ribbon electrode, a paddle electrode, a braided or woven electrode, a mesh electrode, a directional electrode, a patch electrode or another type of electrode configured to deliver a cardioversion/defibrillation shock to heart 26 of patient 12.

In one configuration, defibrillation electrodes 28 are spaced approximately 0.25-4.5 cm, and in some instances between 1-3 cm apart from each other. In another configuration, defibrillation electrodes 28 are spaced approximately 0.25-1.5 cm apart from each other. In a further configuration, defibrillation electrodes 28 are spaced approximately 1.5-4.5 cm apart from each other.

In the configuration shown in FIGS. 1A-1C, defibrillation electrodes 28 span a substantial part of distal portion 16. Each of defibrillation electrodes 28 may be between approximately 1-10 cm in length, between approximately 2-6 cm in length, or between approximately 3-5 cm in length. However, lengths of greater than 10 cm and less than 1 cm may be utilized in accordance with the techniques of this disclosure. A total length of defibrillation electrode on distal portion 16, e.g., length of the two defibrillation electrodes 28 combined, may vary depending on a number of variables. In one example, the total length may be between approximately 5-10 cm. However, the defibrillation electrodes 28 may have a total length less than 5 cm and greater than 10 cm in other embodiments. In some instances, defibrillation electrodes 28 may be approximately the same length or, alternatively, different lengths.

Defibrillation electrodes 28 may be electrically connected to one or more conductors, which may be disposed in the body wall of lead body 13 or in one or more insulated lumens (not shown) defined by lead body 13. In an example configuration, each of defibrillation electrodes 28 is connected to a common conductor such that a voltage may be applied simultaneously to all defibrillation electrodes 28 to deliver an anti-tachyarrhythmia shock to heart 26. In other configurations, defibrillation electrodes 28 may be attached to separate conductors such that each defibrillation electrode 28 may apply a voltage independent of the other defibrillation electrodes 28. In this case, ICD 9 or lead 10 may include one or more switches or other mechanisms to electrically connect the defibrillation electrodes together to function as a common polarity electrode such that a voltage may be applied simultaneously to all defibrillation electrodes 28 in addition to being able to independently apply a voltage.

Distal portion 16 may also include one or more pacing and/or sensing electrodes configured to deliver pacing pulses to heart 26 and/or sense electrical activity of heart 26. Such electrodes may be referred to as pacing electrodes, sensing electrodes, or pace/sense electrodes. In the example illustrated by FIGS. 1A-1C, distal portion 16 includes two pace/sense electrodes 32*a* and 32*b* (collectively, "pace/sense electrodes 32").

In the illustrated example, pace/sense electrode 32*b* is positioned between defibrillation electrodes 28, e.g., within a gap between the defibrillation electrodes, and pace/sense electrode 32*a* is positioned more proximal along distal portion 16 than proximal defibrillation electrode 28*a*. In some examples, more than one electrode 32 may exist within the gap between defibrillation electrodes 28. In some examples, an electrode 32 is additionally or alternatively located distal of the distalmost defibrillation electrode 28*b*.

In one example, the distance between the closest defibrillation electrode 28 and electrodes 32 is greater than or equal to approximately 2 mm and less than or equal to approximately 1.5 cm. In another example, electrodes 32 may be spaced apart from the closest one of defibrillation electrodes 28 by greater than or equal to 5 mm and less than or equal to 1 cm. In a further example, electrodes 32 may be spaced apart from the closest one of defibrillation electrodes 28 by greater than or equal to 6 mm and less than or equal to 8 mm.

Electrodes 32 may be configured to deliver low-voltage electrical pulses to the heart or may sense a cardiac electrical activity, e.g., depolarization and repolarization of the heart. As such, electrodes 32 may be referred to herein as pace/sense electrodes 32. In one configuration, electrodes 32 are ring electrodes. However, in other configurations electrodes 32 may be any of a number of different types of electrodes, including ring electrodes, short coil electrodes, paddle electrodes, hemispherical electrodes, or directional electrodes. Each of electrodes 32 may be the same or different types of electrodes as others of electrodes 32. Electrodes 32 may be electrically isolated from an adjacent defibrillation electrode 28 by including an electrically insulating layer of material between electrodes 32 and adjacent defibrillation electrodes 28. Each electrode 32 may have its own separate conductor such that a voltage may be applied to or sensed via each electrode independently from another electrode 32.

Electrodes 28 are referred to as defibrillation electrodes, and electrodes 32 are referred to as pace/sense electrodes, because they may have different physical structures enabling different functionality. Defibrillation electrodes 28 may be larger, e.g., have greater surface area, than pace/sense electrodes 32 and, consequently, may be configured to deliver anti-tachyarrhythmia shocks that have relatively higher voltages than pacing pulses. The relatively smaller size of pace/sense electrodes 32 may provide advantages over defibrillation electrodes for delivering pacing pulses and sensing intrinsic cardiac activity, e.g., lower pacing capture thresholds and/or better sensed signal quality. Nevertheless, a defibrillation electrode 28 may be used to deliver pacing pulses and/or sense electrical activity of the heart, such as in combination with a pace/sense electrode 32.

In the configuration shown in FIGS. 1A-1C, each electrode 32 is substantially aligned along a major longitudinal axis ("x"). In one example, the major longitudinal axis is defined by a portion of elongate body 13, e.g., substantially linear portion 20. In another example, the major longitudinal axis is defined relative to the body of the patient, e.g., along the anterior median line (or midsternal line), one of the sternal lines (or lateral sternal lines), left parasternal line, or other line.

In one configuration, the midpoint of each electrode 32*a* and 32*b* is along the major longitudinal axis "x," such that each electrode 32*a* and 32*b* is at least disposed at substantially the same horizontal position when the distal portion is implanted within the patient. In some examples, the longitudinal axis "x" may correspond to a caudal-cranial axis of the patient and a horizontal axis orthogonal to the longitudinal axis "x" may correspond to a medial-lateral axis of the patient. In other configurations, the electrodes 32 may be disposed at any longitudinal or horizontal position along the distal portion 16 disposed between, proximal to, or distal to the defibrillation electrodes 28. In the example illustrated in FIG. 1A, electrodes 32 are disposed along the undulating configuration of distal portion 16 at locations that will be closer to heart 26 of patient 12 than defibrillation electrodes 28 (e.g., at a peak of the undulating configuration that is toward the left side of the sternum). As illustrated in FIG. 1A, for example, electrodes 32 are substantially aligned with one another along the left sternal line. In the example illustrated in FIG. 1A, defibrillation electrodes 28 are disposed along peaks of the undulating configuration that extend toward a right side of the sternum away from the heart. This configuration places pace/sense electrodes 32 at locations closer to the heart than electrodes 28, to facilitate cardiac pacing and sensing at relatively lower amplitudes.

In some examples, pace/sense electrodes 32 and the defibrillation electrodes 28 may be disposed in a common plane when distal portion 16 is implanted extracardiovascularly. In other configurations, the undulating configuration may not be substantially disposed in a common plane. For example, distal portion 16 may define a concavity or a curvature.

Proximal end 14 of lead body 13 may include one or more connectors 34 to electrically couple lead 10 to ICD 9. ICD 9 may also include a connector assembly that includes electrical feedthroughs through which electrical connections are made between the one or more connectors 34 of lead 10 and the electronic components included within the housing. The housing of ICD 9 may house one or more processors, memories, transmitters, receivers, sensors, sensing circuitry, therapy circuitry, power sources (capacitors and batteries), and/or other components. The components of ICD 9 may generate and deliver electrical therapy such as anti-tachycardia pacing, cardioversion or defibrillation shocks, post-shock pacing, and/or bradycardia pacing.

The undulating configuration of distal portion 16 and the inclusion of electrodes 32 between defibrillation electrodes 28 provides a number of therapy vectors for the delivery of electrical therapy to the heart. For example, at least a portion of defibrillation electrodes 28 and one of electrodes 32 may be disposed over the right ventricle, or any chamber of the heart, such that pacing pulses and anti-tachyarrhythmia shocks may be delivered to the heart. The housing of ICD 9 may be charged with or function as a polarity different than the polarity of the one or more defibrillation electrodes 28 and/or electrodes 32 such that electrical energy may be delivered between the housing and the defibrillation electrode 28 and/or electrode 32 to the heart.

Each defibrillation electrode 28 may have the same polarity as every other defibrillation electrode 28 when a voltage is applied to it such that a shock may be delivered from all defibrillation electrodes together. In examples in which defibrillation electrodes 28 are electrically connected to a common conductor within lead body 13, this is the only configuration of defibrillation electrodes 28. However, in other examples, defibrillation electrodes 28 may be coupled to separate conductors within lead body 13 and may therefore each have different polarities such that electrical energy may flow between defibrillation electrodes 28, or between one of defibrillation electrodes 28 and one of pace/sense electrodes 32 or the housing electrode, to provide anti-tachyarrhythmia shock, pacing therapy, and/or to sense cardiac depolarizations. In this case, defibrillation electrodes 28 may still be electrically coupled together, e.g., via one or more switches within ICD 9, to have the same polarity.

In some examples, ICD system 8 may include one or more shields 30. Shield 30 may be configured to be implanted in patient 12 separately from implantable lead 10 and/or distal portion 16 of lead 10. Shield 30 may be configured to impede an electric field from delivery of an electrical therapy via an electrode, e.g., from a pacing pulse and/or an anti-tachyarrhythmia shock, in a direction from the electrode away from the heart, e.g., in an anterior direction. In this manner, shield 30 may reduce the likelihood that the electrical field will stimulate extracardiac tissue, such as sensory or motor nerves. Furthermore, shield 30 may direct the electrical field toward the heart, allowing lower energy level pacing pulses to capture the heart and/or lower energy level anti-tachyarrhythmia shocks, than may be required without shield 30. Lower energy pacing pulses may also reduce the likelihood that pacing pulses delivered via the pace electrode or defibrillation pulses delivered via defibrillation electrodes 28 stimulate extracardiac tissue, and may result in less consumption of the power source of ICD 9 and, consequently, longer service life for the ICD. It should be understood that various aspects of the techniques of this disclosure may be applied to implantable systems other than ICD 9, including, but not limited to, bradycardia pacemaker systems. For example, a lead that does not include defibrillation electrodes 28 may include one or more shields 30 and may be used with a pacemaker system without defibrillation capabilities.

In the examples shown, shield 30 is implanted in the pleural cavity of patient 12, e.g., bounded laterally by pleurae 39, posteriorly by pericardium 38, and anteriorly by the sternum 22, and positioned anterior to distal portion 16. In some examples, shield 30 may be implanted such that at least a portion of shield 30 is position between the heart and lung (or lungs) of patient 12, e.g., between pericardium 38 and pleurae 39 of patient 12.

Figure 2A:
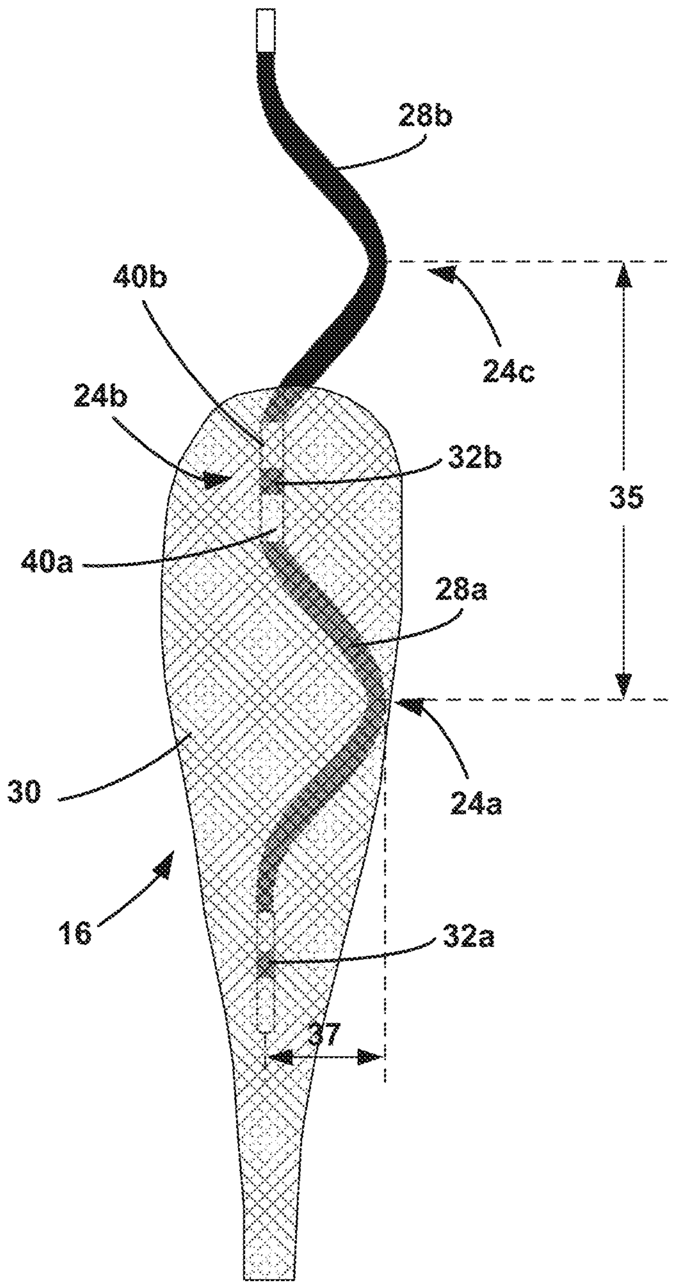
FIG. 2A is a conceptual diagram illustrating a distal portion of an example implantable medical lead and a separately implantable shield of a medical device system.
Figure 2B:
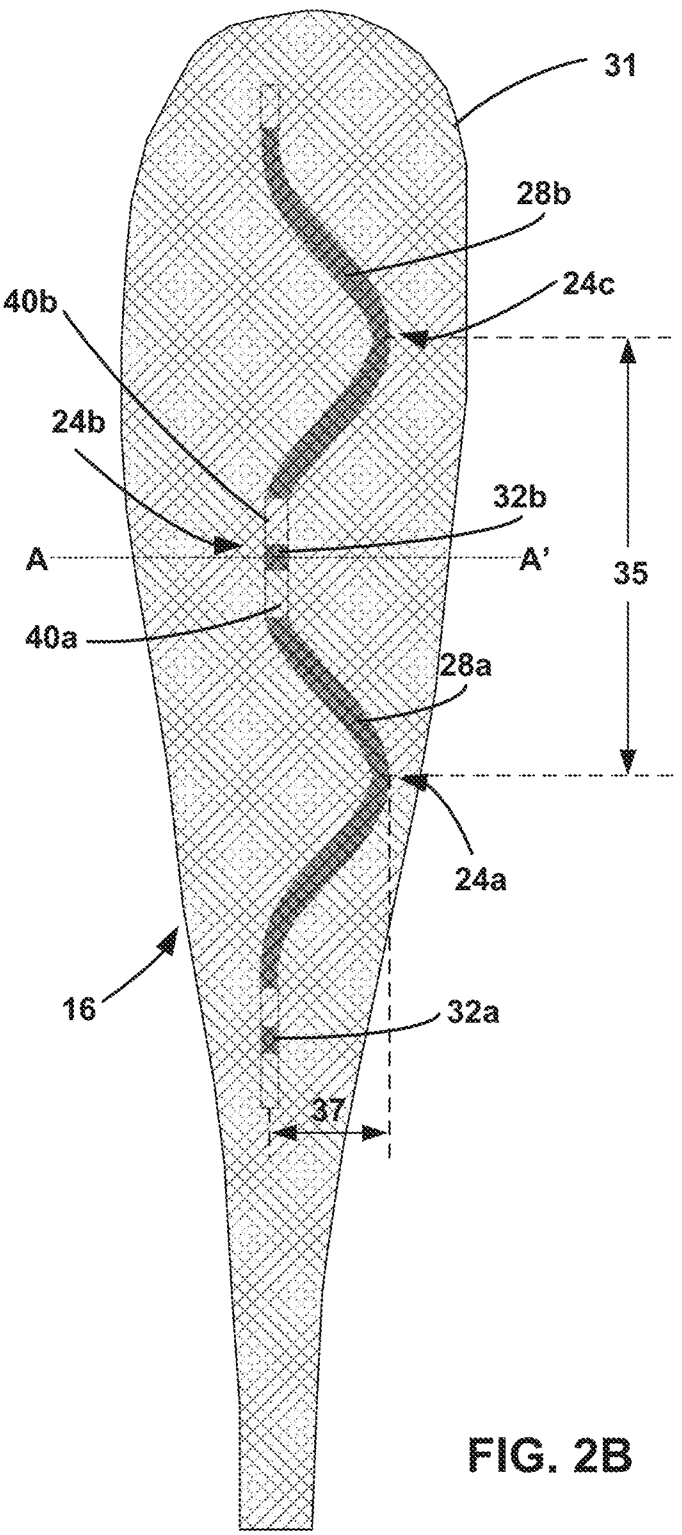
FIG. 2B is a conceptual diagram illustrating a distal portion of an example implantable medical lead and another example separately implantable shield of a medical device system.
Figure 2C:
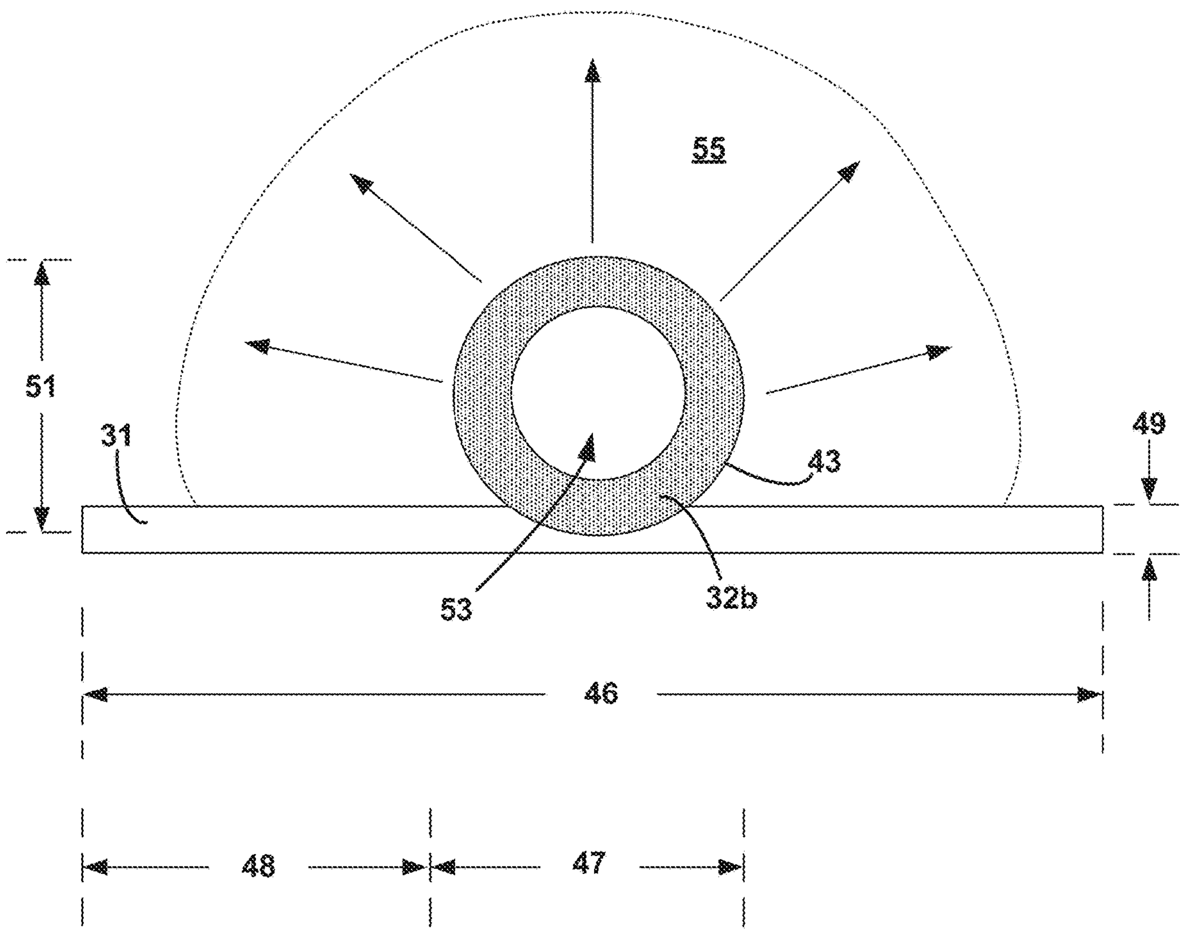
FIG. 2C is a conceptual, cross-sectional view of an electrode of an example implantable medical lead and a separately implantable shield.

FIGS. 2A-2C are conceptual diagrams illustrating views of shield 30 and distal portion 16 of implantable medical lead 10. In particular, FIGS. 2A and 2B illustrate a "top" view in the posterior direction, e.g., shield 30 is anterior to distal portion 16 and is illustrated as being "over" or "on top of" distal portion 16 in the view shown. FIG. 2C is a cross-sectional view taken at line A-A' in FIG. 2B.

FIG. 2A is a conceptual diagram illustrating an example configuration of distal portion 16 of implantable medical lead 10 and a separately implantable shield 30 of a medical device system, e.g., ICD system 8. FIG. 2B is a conceptual diagram illustrating an example configuration of distal portion 16 of implantable medical lead 10 and a separately implantable shield 31 of a medical device system, and is described below together with FIG. 2A.

As illustrated in FIGS. 2A and 2B, the undulating configuration of distal portion 16 may include a plurality of peaks along the length of the distal portion. In the example illustrated by FIG. 2, distal portion includes three peaks 24*a*, 24*b*, and 24*c* (collectively, "peaks 24"). Other configurations, however, may include any number of peaks 24. In the example shown in FIG. 2A, a portion of distal portion 16 is illustrated as being overlapped by shield 30, and in the example shown in FIG. 2B, all of distal portion 16 is illustrated as being overlapped by shield 31. For example, FIG. 2A illustrates distal portion 16 positioned as implanted and separately implantable shield 30 positioned anterior, relative to patient 12 and as implanted, to the portion of distal portion 16 including peaks 24*b* and 24*c*, while FIG. 2B illustrates separately implantable shield 31 positioned anterior to at least all of distal portion 16.

The undulating configuration may define a peak-to-peak distance 35, which may be variable or constant along the length of distal portion 16. In the configuration illustrated in FIGS. 1A-2B, the undulating configuration defines a substantially sinusoidal configuration, with a constant peak-to-peak distance 35 of approximately 2.0-5.0 cm. The undulating configuration may also define a peak-to-peak width 37, which may also be variable or constant along the length of the undulating configuration. In the configuration illustrated in FIGS. 1-2, the undulating configuration defines a substantially sinusoidal shape, with a constant peak-to-peak width 37 of approximately 0.5-2.0 cm. However, in other instances, the undulating configuration may define other shapes and/or patterns, e.g., S-shapes, wave shapes, or the like.

Defibrillation electrodes 28 may extend along, e.g., be disposed on or cover, a substantial part of the undulating configuration of distal portion 16, e.g., along at least 80% of the undulating portion. Defibrillation electrodes 28 may extend along more or less than 80% of the undulating configuration. As another example, defibrillation electrodes 28 may extend along at least 90% of the undulating configuration.

Defibrillation electrode 28*a* extends along a substantial portion of the undulating configuration of distal portion 16 from the proximal end to peak 24*b*, e.g., along a substantial portion of the first "wave" associated with peak 24*a*, and the defibrillation electrode segment 28*b* extends along a substantial portion of the undulating configuration from peak 24*b* to the distal end of the undulating configuration, e.g., along a substantial portion of the second "wave" associated with peak 24*c*). In the example illustrated in FIGS. 1-2, a part of the undulating configuration on which defibrillation electrodes 28 are not disposed is a gap between defibrillation electrodes 28*a* and 28*b*, on peak 24*b*, where electrode 32*b* is disposed.

In the example shown in FIG. 2A, shield 30 covers or is otherwise disposed over a portion of an outer surface of defibrillation electrode 28*a* and pace/sense electrode 32*b*. Shield 30 does not cover an entirety of the outer surface of defibrillation electrode 28*a* or pace/sense electrode 32*b*, e.g., such as surfaces of defibrillation electrode 28*a* and pace/sense electrode 32*b* having a surface normal in the posterior direction. In the example shown in FIG. 2B, shield 31 covers or is otherwise disposed over a portion of an outer surface of defibrillation electrode 28*a*, defibrillation electrode 28*b*, and pace/sense electrode 32*b*. Shield 31 does not cover an entirety of the outer surface of defibrillation electrode 28*a*, defibrillation electrode 28*b*, or pace/sense electrode 32*b*, e.g., such as surfaces of defibrillation electrode 28*a*, defibrillation electrode 28*b*, and pace/sense electrode 32*b* having a surface normal in the posterior direction.

Pacing pulses delivered by ICD 9 via pace/sense electrodes 32*a* and 32*b*, and anti-tachyarrhythmia shocks delivered by ICD 9 via defibrillation electrodes 28*a* and 28*b*, result in an electrical field proximate the electrode, that "spreads" from the electrode surface toward one or more other electrodes used to deliver the pacing pulse. Shields 30 and 31 impedes the electrical field in directions from the electrode toward the shield, and allows the spread in directions from the electrodes away from the shield. In this manner, shield 30 is configured to make electrodes 28 and 32 directional.

As illustrated in both FIGS. 2A and 2B, shields 30 and 31 may extend laterally away from electrodes 28 and 32, e.g., in a substantially planar manner, such that the dimensions of shield 30 in a plane are greater than those of electrodes 28 and 32 in the plane. In this manner, shields 30 and 31 may further (or more effectively) limit the directions, e.g., radial angles, of the spread of the electrical field generated by electrodes 28 and 32. The plane in which shields 30 and 31 extends laterally from electrodes 28 and 32 may be the same plane in which peaks 24 of the undulating configuration extend, or a substantially parallel plane.

The portion of the outer surface of electrodes 28 and 32 over which shields 30 and 31 are positioned may be referred to as an "anterior portion" of the outer surface of electrodes 28 and 32, since that portion of electrodes 28 and 32 may be more anteriorly positioned within patient when distal portion 16 of lead 10 is implanted within patient, e.g., patient 12. With shield 30 or 31 positioned over an anterior portion of the outer surface of one or more of electrodes 28 and/or 32, shield 30 or 31 may be positioned anteriorly relative to the central longitudinal axis of electrodes 28 and/or 32. With shield 30 or 31 positioned over an anterior portion of the outer surface of electrodes 28 and 32, and distal portion 16 implanted within the patient as illustrated in FIGS. 1A-1C, shield 30 or 31 may impede the electrical field in directions away from heart 26, referred to as anterior directions.

Shield 30 and/or 31 may be electrically insulative. In some examples, shield 30 and/or 31 comprises a polymer, such as polyurethane. In some examples, shield 30 and/or 31 is configured to be implanted in patient 12 separately from the implantable medical lead 10 and disposed anterior at least one of electrodes 28 and 32, e.g., via a shield implant tool such as shield implant tool 400 of FIG. 4 and/or shield implant tool 500 of FIG. 5. In some examples, shield 30 and/or 31 comprises elastic or super-elastic polymer or metallic structures, e.g., Nitinol structures, to facilitate the deployment of shield 30 and/or 31, support articulation of shield 30 and/or 31, and/or support shield 30 and/or 31 in the deployed, relaxed (e.g., implanted) configuration. The deployed and/or articulated configuration may be substantially planar, as illustrated in FIGS. 2A and 2B, or may be non-planar. For example, portions of shield 30 and/or 31 spaced further away laterally from electrodes 28 and/or 32 may be situated more posteriorly than portions closer to the electrode, e.g., in the shape of a cup or bowl.

Such support structures may be partially or fully embedded within a primary material of shield 30 and/or 31, or attached to one or more outer surfaces of shield 30 and/or 31. In some examples, a support structure is located circumferentially around a perimeter of shield 30 and/or 31, e.g., spaced a greatest distance laterally from the shield. However, other support structure locations are possible. For example, one or more support structures may extend in radial or lateral direction from the electrode, e.g., from near electrode to near a periphery of the shield.

As illustrated in FIGS. 2A and 2B, distal portion 16 of lead 10 may include lead body portion 40*a* and lead body portion 40*b* (collectively, "lead body portions 40"). Lead body portions 40 extend between pace/sense electrode 32*b* and a respective one of defibrillation electrodes 28. Lead body portions 40 may provide a relatively even or smooth surface transition between the outer profile of pace/sense electrode 32*b* and the outer profiles of defibrillation electrodes 28. Conductors coupled to electrodes 32*b* and 28*b* may extend through lead body portion 40*a*, and a conductor coupled to electrode 28*b* may extend through lead body portion 40*b*. Lead body portions 40*a* and 40*b* may formed of one or more polymers, which may be the same as or different from shields 30 and 31, and/or other portions of lead body 13.

As illustrated in FIG. 2C, pace/sense electrode 32*b* may define a lumen 53, e.g., may be in the form of a ring, and a conductor coupled to electrode 28*b* may extend through lumen 53. Although illustrated in FIG. 3C as a ring, pace/sense electrodes 32 may have other shapes, including partial or segmented ring shapes or arc shapes, in which one or more electrodes or electrode segments extend less than 360-degrees around a circumference of the lead.

Because shields 30 and 31 only cover an anterior portion of outer surface of one or more of electrodes 28 and/or 32 (e.g., surface 43 of pace/sense electrode 32*b* in the example shown), a depth 49 of shields 30 and 31 may be less than a depth of electrodes 28 and/or 32 (e.g., depth 51 of pace/sense electrode 32*b* in the example shown), such as less than one half of the depth of any of electrodes 28 and/or 32. Although illustrated as substantially constant, depth 49 of shield 31 (or shield 30, not shown) may vary. For example, depth 49 may increase toward electrodes 28 and/or 32, and/or decrease toward an edge of the shields 30 or 31, e.g., to provide a smooth or otherwise desired transition between shields 30 or 31 and electrodes 28 and/or 32, and/or between shields 30 or 31 and tissue of the patient. Additionally, although defibrillation electrodes 28, pace/sense electrodes 32, and lead body portions 40*a* and 40*b* are shown in FIG. 2B as having substantially equal depths (e.g., circumferences) that are greater than depth 49 of shield 31, in other examples depth 49 of shields 30 or 31 may be similar to that of lead body portions 40*a* and 40*b* and pace/sense electrode 32*b* may extend outward from lead body portions 40*a* and 40*b* and shields 30 or 31, e.g., due to having a greater depth or being offset from a longitudinal axis defined by lead body portions 40*a* and 40*b*.

As illustrated in FIG. 2C, pacing pulses delivered by ICD 9 via pace/sense electrode 32*b* result in an electrical field 55 proximate the electrode, that "spreads" from electrode outer surface 43. Similarly, although not shown, anti-tachyarrhythmia shocks delivered by ICD 9 via defibrillation electrodes 28 result in an electric field proximate the electrode that spreads from the electrode outer surface similar to that shown for pace/sense electrode 32*b*. Shields 30 and/or 31 may reduce and/or impede the electrical field in directions from the electrode toward the shield, and allows the spread in directions from the electrode away from the shield. In this manner, shields 30 and/or 31 are configured to make any or all of pace/sense electrodes 32 and defibrillation electrodes 28 directional.

Figure 3A:
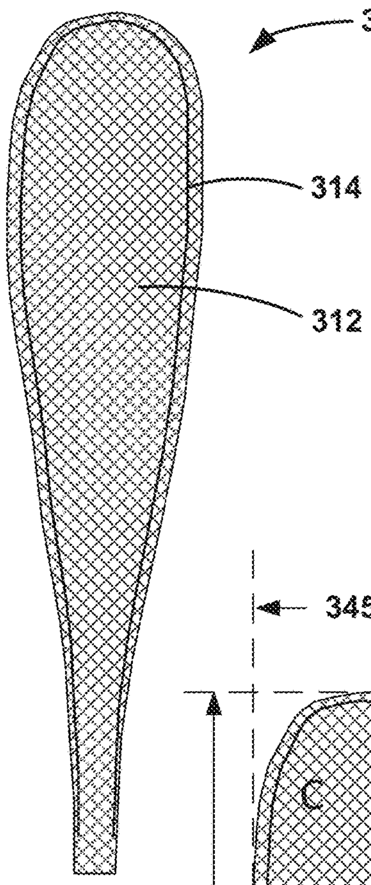
FIG. 3A is a conceptual diagram illustrating a view of an example shield of an implantable medical device system.
Figure 3C:
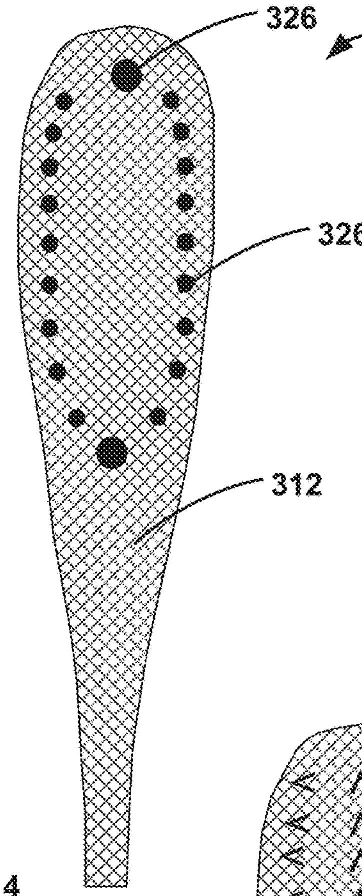
FIG. 3C is a conceptual diagram illustrating a view of another example shield of an implantable medical device system.
Figure 3B:
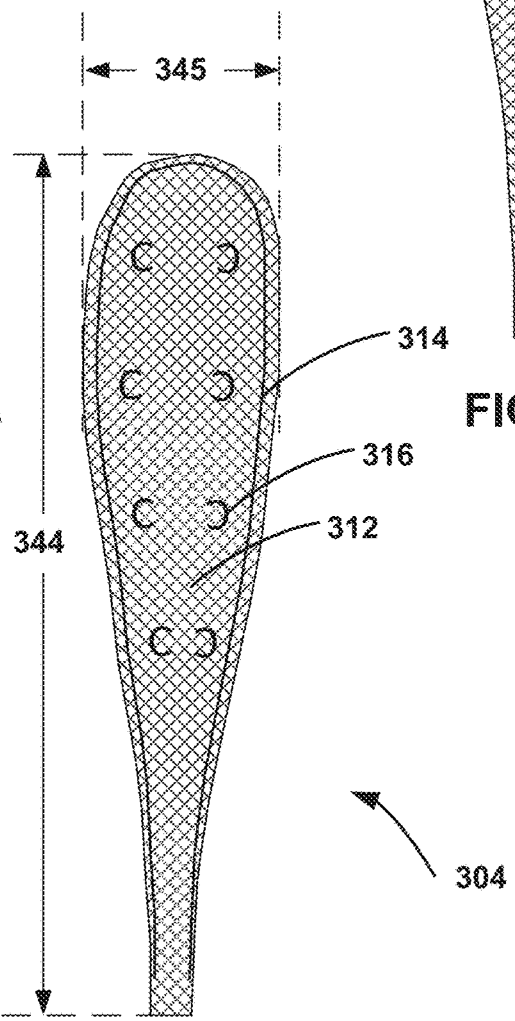
FIG. 3B is a conceptual diagram illustrating a view of another example shield of an implantable medical device system.
Figure 3D:
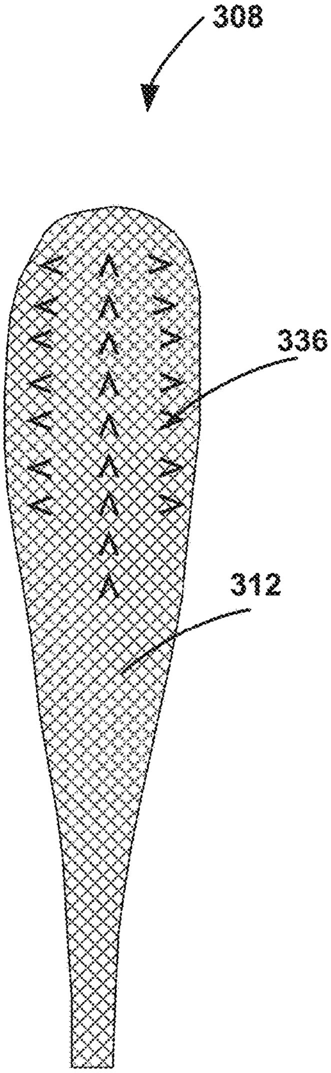
FIG. 3D is a conceptual diagram illustrating a view of another example shield of an implantable medical device system.

FIGS. 3A-3D are conceptual diagrams illustrating differing example shields 302-308 of an implantable medical device system. FIG. 3A is a conceptual diagram illustrating an example shield 302 including perimeter structure 314, FIG. 3B is a conceptual diagram illustrating an example shield 304 including radiopaque markers 326, FIG. 3C is a conceptual diagram illustrating an example shield 306 including radiopaque markers 336, and FIG. 3D is a conceptual diagram illustrating an example shield 308 including perimeter structure 314. In the examples shown, each of shields 302-308 include shield body 312.

Shield body 312 defines the overall shape of the shield, e.g., any of shields 30, 302-308 described herein. Shield body 312 may be electrically insulative and comprises of a polymer, such as polyurethane, or any suitable electrically insulative material. Shield body 312 may comprise a mesh structure, a woven structure, a non-woven structure, or any suitable structure and material combination suitable to form an electrically insulative area and/or volume. In some examples, shield body 312 may include one or more coatings, e.g., a coating of a biocompatible and nonconductive material. In some examples, shield body 312 may comprise an insulating ceramic film, a ceramic coated flexible mesh, a semiconductor film, or any flexible and electrically insulating film.

In some examples, shield body 312 may comprise a mesh structure configured to stretch substantially in a single direction, e.g., a uniaxial and/or anisotropic stretch configured to stretch along the major longitudinal axis "x" of FIG. 1A (e.g., the central longitudinal axis of electrodes 28 and/or 32). The mesh structure may be a carrier for the insulative material and/or polymer of shield body 312. Shield body 312 may be configured to have an improved removability, e.g., via the uniaxial stretch which may enable shield body 312 to peel through any scar tissue. In some examples, shield body 312 may comprise a mesh structure configured to stretch uniaxially substantially perpendicularly to the central longitudinal axis of electrodes 28 and/or 32, e.g., a "horizontal" stretch. In some examples, shield body 312 with a uniaxial horizontal stretch may be configured to have an improved ease of placement, e.g., via an increased rigidity in in the "vertical" direction (e.g., along the central longitudinal axis of electrodes 28 and/or 32).

In the example of FIG. 3A, shield 302 includes shield body 312 and perimeter structure 314. Perimeter structure 314 is disposed proximally to at least a portion of the edge and/or edges of shield body 312. In some examples, perimeter structure 314 is configured to provide support to keep the desired shape of shield body 312. For example, shield body 312 may be made of a relatively thin, flexible material, and perimeter structure 314 may be configured to prevent shield body 312 from folding, kinking, curling, or otherwise not keeping its intended shape, or extending to its intended full area/volume, when implanted. In the example shown, shield body 312 has a substantially ovoid shape with an elongated portion or "tail." The ovoid shape may be configured for sufficient spatial electrical insulation to reduce electrical fields/conduction in an anterior direction and the tail portion may be configured to extend towards an incision site on the patient to ease/facilitate removal and/or manipulation of any of shields 302-308. In other examples, shield body 312 (e.g., and shields 302-308) may have any suitable shape configured for sufficient spatial electrical insulation to reduce electrical fields/conduction in an anterior direction.

In some examples, perimeter structure 314 may include a material having sufficient elasticity or shape memory, e.g., Nitinol. Perimeter structure 314 may be configured to be any or all of radiopaque, corrosion resistant, kink resistant, biocompatible, and flexible/elastic. In some examples, perimeter structure 314 may be platinum, MP35N®, tantalum, Nitinol, or any suitable elastic material. In some examples, perimeter structure 314 may be a coil of platinum, MP35N®, tantalum, Nitinol, or any suitable elastic material, optionally cladded with a biocompatible material such as platinum, platinum-iridium, or any suitable biocompatible material. Perimeter structure 314 may be bonded and/or attached to a surface of shield body 312, or perimeter structure 314 may be bonded and/or attached at least partially within shield body 312, e.g., at least partially within the thickness of the material/structure of shield body 312. In some examples, perimeter structure 314 may be encased via lamination of a material to shield body 312, e.g., encased and held to shield body 312 via lamination of a polyurethane to shield body 312 over perimeter structure 314.

In some examples, perimeter structure 314 may be a radiopaque marker and/or an edge marker extending along an outer perimeter of shield 302 (e.g., shield body 312), and may be configured to aid in implanting/positioning shield 302. For example, perimeter structure 314 may be configured to indicate and/or allow a user to visualize at least one of a position or an orientation of shield body 312 (and/or shield 302) within the patient by identification of the radiopaque markers in a fluoroscopic or other image.

In the example of FIG. 3B, shield 304 includes shield body 312 and radiopaque markers 316. Shield 304 may be similar to shield 302 described above with the addition of radiopaque markers 316. Shield 304 may include any number of radiopaque markers 316. Radiopaque markers 326 (when more than one) may be distributed symmetrically or asymmetrically (e.g., relative to electrodes 28, 32) on a surface of, or within, shield body 312. Radiopaque markers 316 may be positioned about shield 304 to allow a user to visualize at least one of a position or an orientation of shield 304 within the patient by identification of the radiopaque markers in a fluoroscopic or other image. In some examples, each of radiopaque markers 316 may be the same as each other or be different from each other in one or more ways, e.g., size, shape, or orientation, to allow, for example, a physician to differentiate between radiopaque markers 316 for facilitating visualization of the orientation of shield 304. For example, one or more of a plurality of radiopaque markers 304 may be larger than the rest such that the physician may determine, based on the position of the larger radiopaque marker 316 (e.g., relative to other radiopaque markers 316), the orientation of shield 304.

In the example of FIG. 3C, shield 306 includes shield body 312 and radiopaque markers 326. Shield 306 may include any number of radiopaque markers 326. Radiopaque markers 326 (when more than one) may be distributed symmetrically or asymmetrically (e.g., relative to electrodes 28, 32) on a surface of, or within, shield body 312. Radiopaque markers 326 may be positioned about shield 306 to allow a user to visualize at least one of a position or an orientation of shield 306 within the patient by identification of the radiopaque markers in a fluoroscopic or other image. In some examples, each of radiopaque markers 326 may be the same as each other or be different from each other in one or more ways, e.g., size, shape, or orientation, to allow, for example, a physician to differentiate between radiopaque markers 326 for facilitating visualization of the orientation of shield 306. For example, one or more of a plurality of radiopaque markers 306 may be larger than the rest such that the physician may determine, based on the position of the larger radiopaque marker 326 (e.g., relative to other radiopaque markers 326), the orientation of shield 306.

In the example shown, shield 306 does not include perimeter structure 314 or radiopaque markers 316. For example, shield 306 may be configured to be separately implanted in the patient via an implant tool, which may orient, position, and deploy shield 306 to the desired implant position, orientation, and shape. In other examples, shield 306 may include one or both of perimeter structure 314 and radiopaque markers 316.

In the example of FIG. 3D, shield 308 includes shield body 312 and radiopaque markers 336. Shield 308 may be substantially similar to shield 306 with the difference being different radiopaque markers 336. In the example shown, radiopaque markers are a different shape, e.g., chevrons, from radiopaque markers 326, and the shape of each of radiopaque markers 336 may individually indicate an orientation of each of the radiopaque markers 336. Shield 308 may include any number of radiopaque markers 336, and radiopaque markers 336 (when more than one) may be distributed symmetrically or asymmetrically (e.g., relative to electrodes 28, 32) on a surface of, or within, shield body 312. Radiopaque markers 336 may be positioned about shield 308 to allow a user to visualize at least one of a position or an orientation of shield 306 within the patient by identification of the radiopaque markers and their individual orientation in a fluoroscopic or other image. For example, the individualized orientations of radiopaque markers 336 may allow a user to determine of shield 308 is flipped or not, e.g., with the opposite surface of shield body 312 facing the anterior direction from what was intended.

In the example shown, and similar to shield 306 described above, shield 308 does not include perimeter structure 314 or radiopaque markers 316. For example, shield 308 may be configured to be separately implanted in the patient via an implant tool, which may orient, position, and deploy shield 308 to the desired implant position, orientation, and shape. In other examples, shield 308 may include one or both of perimeter structure 314 and radiopaque markers 316.

In the example shown in FIG. 3B, shield 304 may have a length 344 and a width 345. Each of shields 302, 306, and 308 may have the same length 344 and width 345 as shield 304, or different lengths 344 and widths 345 than shield 304. For convenience, each of shields 302-308 are described below as having length 344 and width 345 as illustrated in FIG. 3B.

The length 344 and width 345 of shields 302-308 may be greater than the length and/or width of any or all of electrodes 28, 32, or distal portion 16, of implantable medical lead 10, e.g., such as at least twice the length and/or width of the undulating shape of distal portion 16.

Figure 3E:
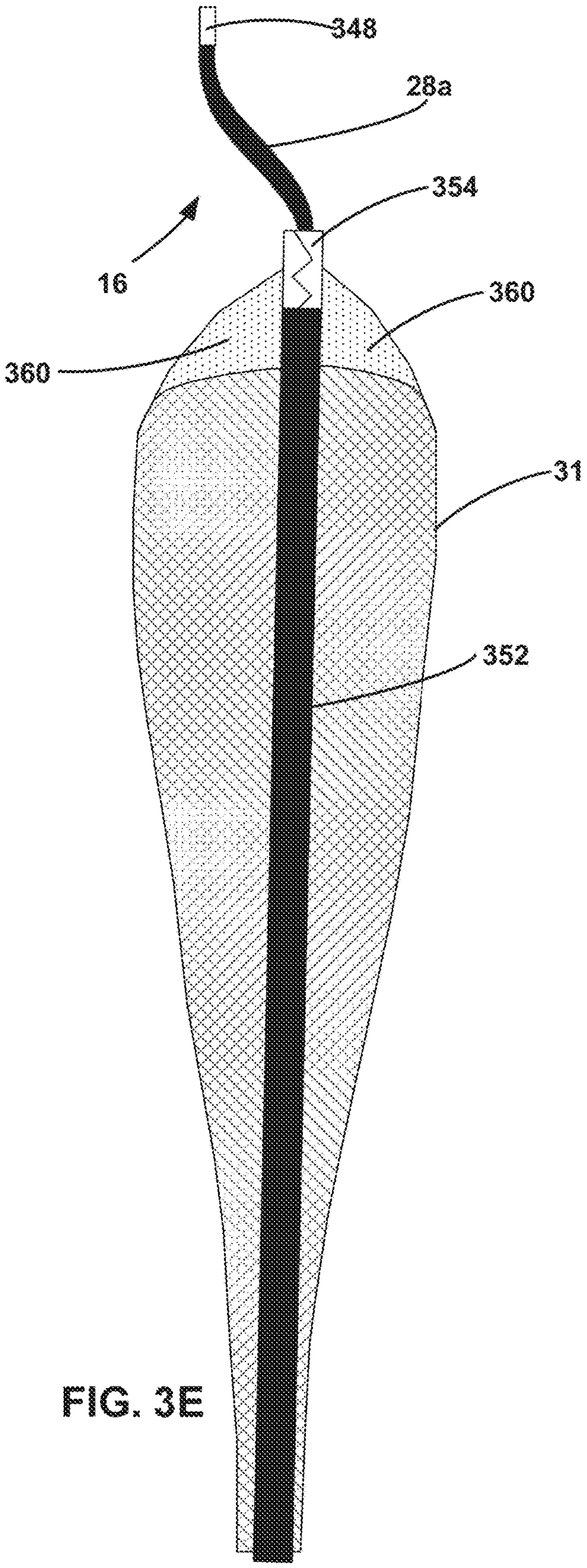
FIG. 3E is a conceptual diagram illustrating a view of an example shield attached to an example implant tool for implantation separate from an example implantable medical lead.
Figure 3F:
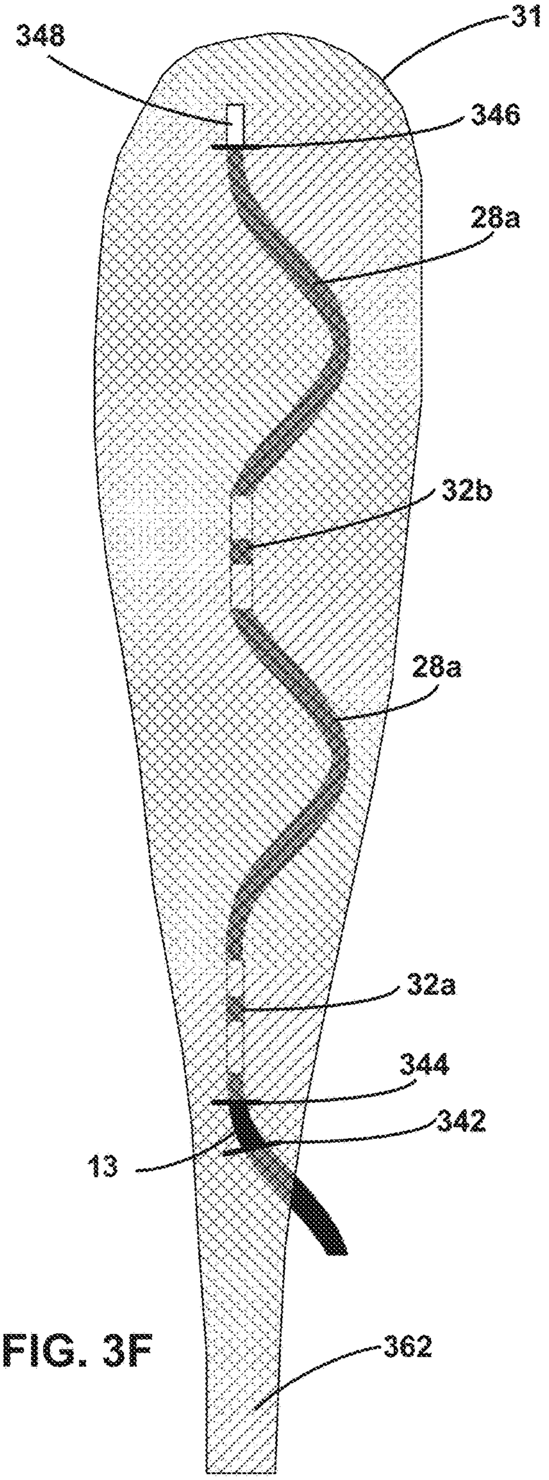
FIG. 3F is a conceptual diagram illustrating a view of an example shield separately implanted and attached to an example implantable medical lead device.

FIG. 3E is a conceptual diagram illustrating a view of an example shield 31 attached to an example implant tool for implantation separate from an example implantable medical lead. FIG. 3F is a conceptual diagram illustrating a view of an example shield separately implanted and attached to an example implantable medical lead device. FIGS. 3E and 3F are described together below.

The example shown in FIG. 3E includes distal portion 16 of implantable medical device 10, shield 31, and implant tool 352. In the example shown, implant tool 352 is configured to separately implant both implantable medical lead 10 and shield 31. In some examples, implant tool 352 is configured to implant implantable medical lead 10 and shield 31 concurrently, and in other examples, implant tool 352 is configured to implant implantable medical lead 10 and shield 31 at different times and/or during different steps of an implant procedure and/or method.

In the example shown, implant tool 352 includes tool distal end 354. Tool distal end 354 includes is configured to couple/attach/grip shield 31, e.g., via a coupling member (not shown) of shield 31. Implant tool 352 may be configured to implant shield 31 when the tool distal end 354 is coupled with shield 31, and implant tool 352 may be configured to deploy shield 31 to its intended final position/orientation. In some examples, tool distal end 354 may comprise a hook, one or more gripping members, a slot, opposing jaws configured to open and close, or any suitable means for coupling to shield 31 and/or a coupling member of shield 31.

Implant tool 352 includes a lumen through which at least distal portion 16 may be delivered to an implant site and/or position. For example, tool distal end 354 may be configured to open, or include an opening, through which at least a portion of implantable medical device 10 or distal portion 16 may be delivered. In the example shown, distal portion 16 is partially delivered/extended from implant tool 352.

In the example shown, tool distal end 354 is coupled with shield 31 in a configuration in which a portion of the distal end of shield 31 is at least partially folded over and/or wrapped onto itself or implant tool 352, e.g., distal portion 360 is in a folded or wrapped configuration. For example, shield 31 may be flexible, and folding over the distal portion 360 of shield 31 may ease insertion/implantation of shield 31. In some examples, shield 31 may be configured to couple to implant tool 352 with distal portion 360 folded over.

In some examples, shield 31 may include one or more slits (e.g., slits 342, 344, and 346 of FIG. 3F) and/or slots configured to allow shield 31 to slide along implantable medical lead 10, e.g., along elongated body 13 and/or distal portion 16, into a final implant position anterior to at least a portion of distal portion 16. In the example shown in FIG. 3E, implant tool 352 may be configured to deliver distal portion 16 and separated grab and/or couple with shield 31 at or near proximal end 14 of lead body 13 and move shield 31 along lead body 13 via lead body 13 being threaded through one or more slits 342, 344, 346. FIG. 3E illustrates shield 31 partially slid along lead body 13 towards its final position.

In the example shown, when shield 31 is in its final implant position, e.g., with slit 346 at or near a proximal end of distal tip 348 of distal portion 16, implant tool 352 may be configured to release distal portion 360 of shield 31 allowing shield 31 to spread out to an open configuration, e.g., as illustrated in FIG. 3F. FIG. 3F illustrates lead body 13 and distal portion 16 attached to shield 31 via threading through slits 342, 344, and 346. For example, distal tip 348 and a portion of lead body 13 between slits 342 and 344 are anterior to shield 31, while shield 31 is anterior to the rest of distal portion 16 and a portion of lead body 13. In some examples, shield 31 may be configured to deploy distal portion 360 to unfold to its full area from the folded position, e.g., via elasticity and/or shape memory, and in other examples implant tool 352 may be configured to position and or orient shield 31, e.g., including distal portion 360, relative to implantable medical lead 10 and/or distal portion 16 and in the open configuration.

In some examples, alternatively or additionally to slits 342, 344, 346, shield 31 may include one or more loops. Implant tool 352 may be configured to slide shield 31 along lead body 13 and/or distal portion 16 via one or more loops, and shield 31 may be configured to attach to lead body 13 and/or distal portion 16 via one or more loops e.g., rather than via slits 342, 344, 346.

In some examples, shield 31 may be substantially similar to shields 302-308. For example, shield 31 may include any or all of perimeter structure 314, radiopaque markers 316, radiopaque markers 326, and radiopaque markers 336. In some examples, shield 30 may be substantially similar to shield 31 described above, e.g., configured to be implanted via implant tool 352 to partially cover/shield distal portion 16 in an anterior direction. For example, shield 30 may include any or all of slits 342, 344, 346, perimeter structure 314, radiopaque markers 316, radiopaque markers 326, and radiopaque markers 336.

Figure 4:
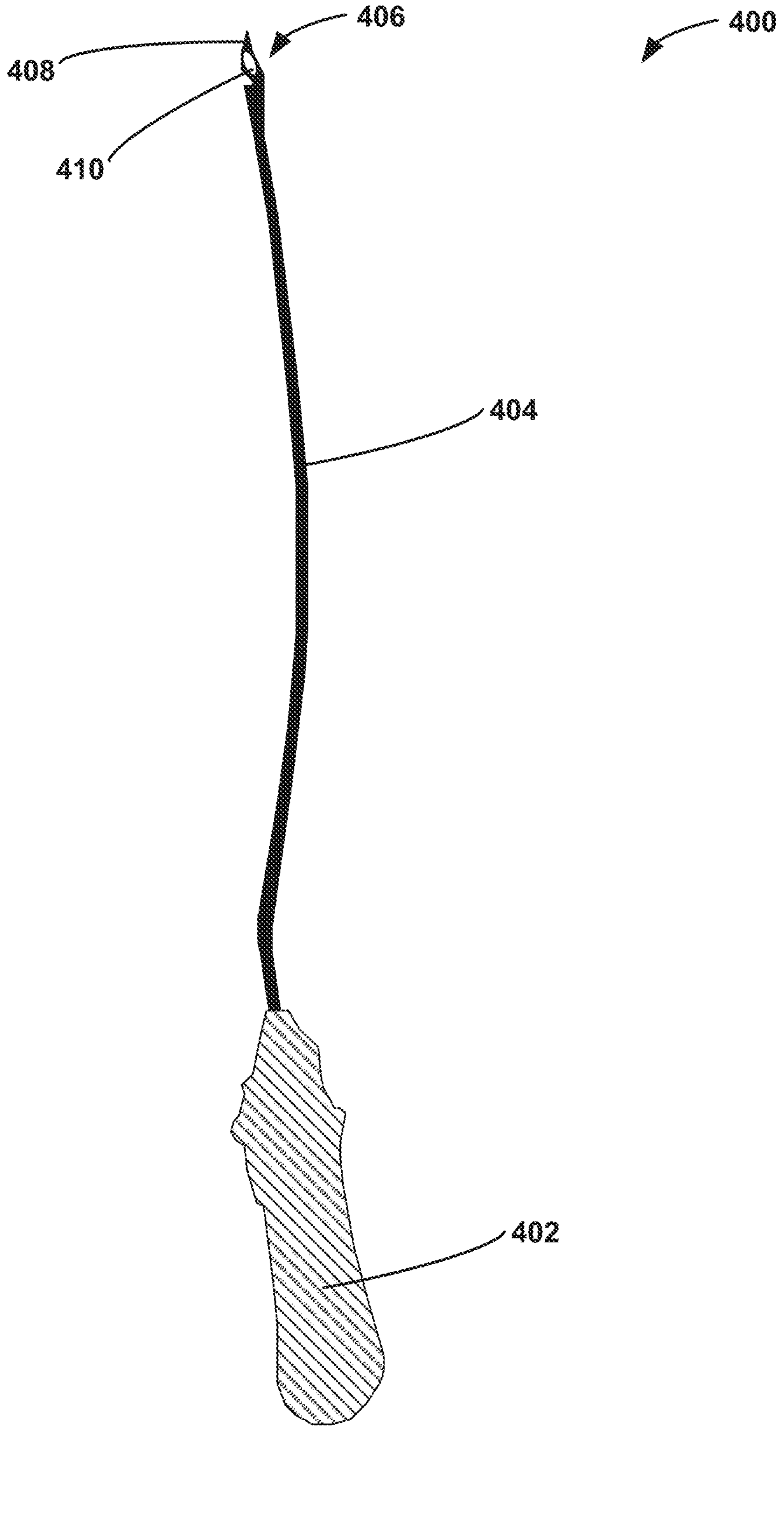
FIG. 4 is a conceptual diagram illustrating an example implant tool.

FIG. 4 is a conceptual diagram illustrating an example shield implant tool 400. Shield implant tool may be substantially similar to shield implant tool 352 described above. In the example shown, shield implant tool 400 includes handle 402, tool body 404, and tool distal end 406. Although implant tool 400 is described below with reference to shield 31, implant tool 400 may be used with, and the description below similarly applies to any of the shields described herein, e.g., shields 30, 31, 302-308.

Handle 402 is configured to allow a user to manipulate implant tool 400 to implant implantable medical lead 10 and/or shield 31. For example, tool body 404 may extend to tool distal end 406. Tool distal end 406 may be configured to couple with any of shield 31, and implant tool 400 may be configured to implant shield 31 when tool distal end 406 is coupled with shield 31. A user may manipulate handle 402 in order to manipulate tool body 404 and tool distal end 406 in order to position and/or orient implantable medical lead 10 and/or shield 31.

In some examples, tool distal end 406 is configured to couple to a coupling member of shield 31. In the example shown, tool distal end 406 includes tool tip 408 and eyelet 410. Tool tip 408 may comprise a hook configured to couple to a coupling member of shield 31, and eyelet 410 may be configured to couple to, or receive, a coupling member of shield 31.

In some examples, implant tool 31 is configured to attach shield 31 to implantable medical lead 10 when implantable medical lead 10 is implanted within a patient. In some examples, implant tool 31 is configured to position and/or orient shield 31 relative to implantable medical lead 10 when implantable medical lead 10 is implanted within the patient. For example, tool distal end 406 may be configured to be coupled to a slit and/or slot in the distal end of shield 31, and to pull shield 31 into place on an anterior side of implantable medical lead 10, e.g., following the implantable medical lead 10 tunneling path through the patient to the implant location/site. In some examples, implantable medical lead 10 may be partially threaded through slits of shield 31 and implant tool 400 may be used to pull shield 31 into place, e.g., using implantable medical lead 10 (such as lead body 13) as a guide. In other examples, shield 31 may be completely separate from implantable medical lead 10 and implant tool 400 may be configured to be used to thread/place shield 31 over implantable medical lead 10 from the distal side of implantable medical lead 10 (e.g., as opposed to sliding shield 31 up lead body 13 from proximal end 14).

In some examples, implant tool 400 may be configured to deploy shield 31, e.g., once shield 31 is in position. For example, implant tool 400 may be configured to be manipulated by a user to decouple and/or disconnect tool distal end 406 from shield 31 and to optionally "wave" implant tool 400 side to side to flatten and/or fully deploy shield 31 in an open configuration anterior to implantable medical lead 10. In some examples, shield 31 may be flexible and/or stretchable, e.g., to aid in stretching shield 31 over and threading implantable medical lead 10 and/or deploying shield 31 to an open configuration. In some examples, implant tool 31 may be configured to position and/or orient shield 31 with a tail portion 362 visible from an incision site, e.g., to ease removal of shield 31.

In some examples, tool body 404 may be shaped in order to implant implantable medical lead 10 and/or shield 31. For example, tool body 404 may have a curved shape in order to navigate implantable medical lead 10 and/or shield 31 through a tunneling path through the patient to the implant location. In some examples, tool body 404 may be flexible enough to navigate the tunneling path while still being rigid enough to pull shield 31 through the tunneling path and manipulate, position, orient, and/or deploy shield 31 at the implant location and/or attach shield 31 to implantable medical lead 10.

Figure 5:
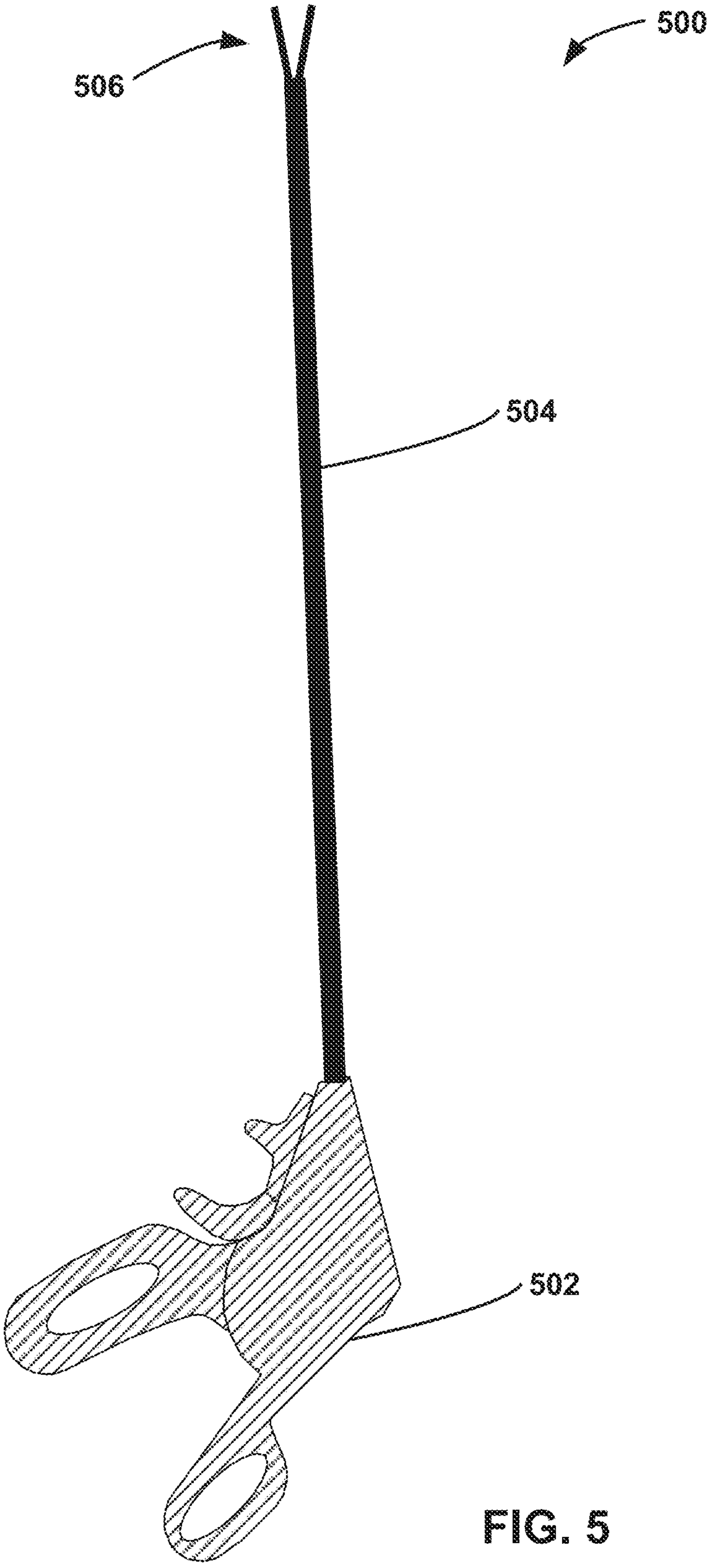
FIG. 5 is a conceptual diagram illustrating another example implant tool.

FIG. 5 is a conceptual diagram illustrating another example implant tool 500. Implant tool 500 may be substantially similar to shield implant tool 352 described above. In the example shown, implant tool 500 includes handle 502, tool body 504, and tool distal end 506. Although implant tool 500 is described below with reference to shield 31, implant tool 500 may be used with, and the description below similarly applies to any of the shields described herein, e.g., shields 30, 31, 302-308.

Handle 502 is configured to allow a user to manipulate implant tool 500 to implant implantable medical lead 10 and/or shield 31, e.g., similar to handle 402 of implant tool 400. Handle 502 may be additionally include a user-manipulable mechanism to control tool distal end to grab and/or release. In the example shown, tool handle 402 includes a trigger mechanism configured to open and/or close opposing jaws of tool distal end 506, e.g., to grip shield 31, a portion of implantable medical lead 10, and/or a coupling member of shield 31 and/or implantable medical lead 10. A user may manipulate handle 502 in order to manipulate tool body 504 and tool distal end 506 in order to position and/or orient implantable medical lead 10 and/or shield 31.

Figure 6:
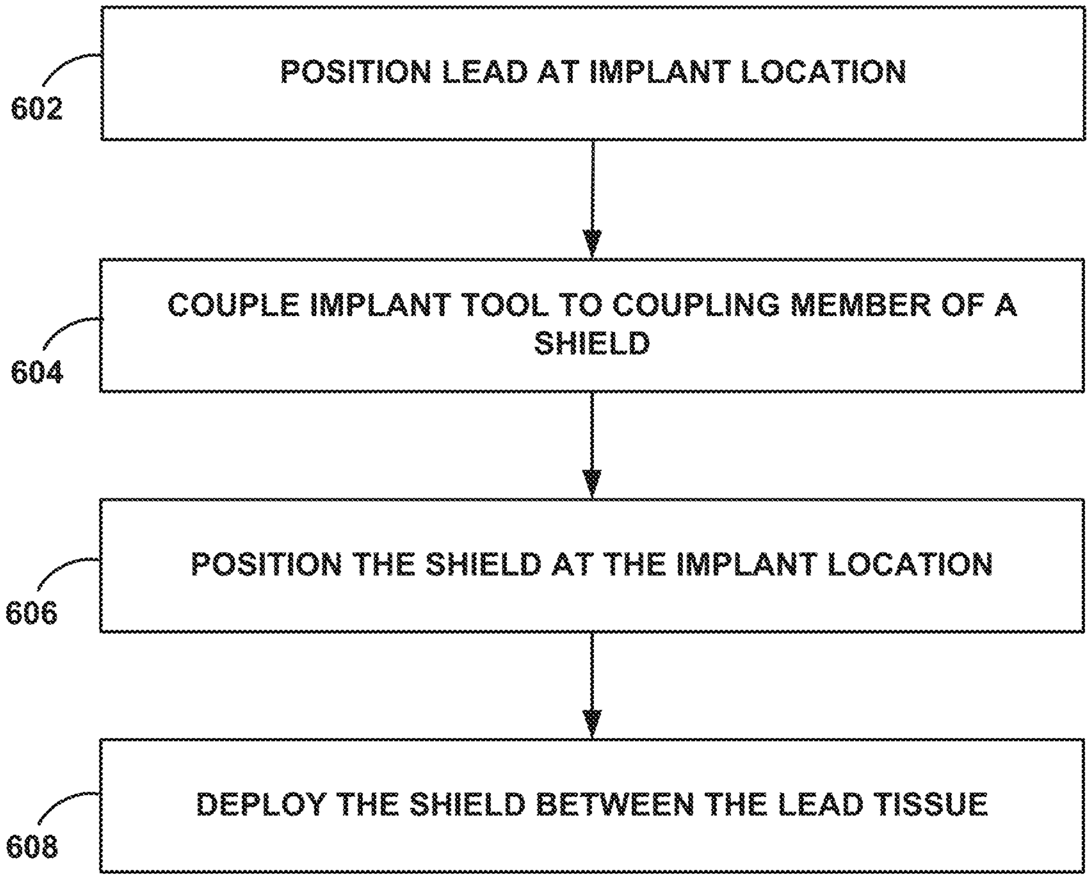
FIG. 6 is a flow diagram illustrating an example technique for implanting an implantable medical lead comprising a shield.

FIG. 6 is a flow diagram illustrating an example technique for implanting a medical device including an implantable medical lead and a separately implantable shield. FIG. 6 is described with respect to implantable medical lead 10, shield 31, and implant tools 352, 400, and 600. However, the example technique of FIG. 4 may be used to implant other leads, shields, or implant tools, e.g., shields 30 and/or 302-308 and other implant tools.

A medical practitioner may position and/or implant distal portion 16 of implantable medical lead 10 into a substernal or other extravascular location using an implant tool (602). In some examples, distal portion 16 may be loaded into the lumen and packaged in a sterile package prior to the implantation procedure, e.g., by a manufacturer of lead 10 and/or the implant tool. The lumen of the implant tool may be cylindrical, or may otherwise have a profile that matches the outer profile of distal portion 16. The undulating configuration of distal portion 16 may be straightened when within the lumen. In one example, the lumen may comprise a sheath. Configurations other than those including a lumen of an implant tool for releasing shield 31 are contemplated by this disclosure.

In some examples, the medical practitioner may introduce the implant tool into the patient via a subxiphoid incision, and advance the implant tool to the extravascular location. Advancement of the tool to the extravascular location may occur before or after implantable medical lead 10 is loaded into the tool. In either case, distal portion 16 of lead 10 is positioned at the extravascular location using the implant tool, e.g., by advancement through the lumen or advancement of the tool while in the lumen. In one embodiment, the implant tool may include a tunneling tool having a rod or other tunneling member and a sheath configured to be placed on the rod. The medical practitioner may removes distal portion 16 of lead 10 from the implant tool to position distal portion 16 at the implantation location and/or site.

In some examples, the medical practitioner may position and orient the shield using an implant tool 400 and/or 500 via one or more radiopaque markers. For example, shield 31 may include radiopaque markers 316, 326 and/or 336 and/or radiopaque components such as perimeter structure 314. The medical practitioner may identify the location, position, orientation (e.g., flipped or not), and/or configuration (e.g., folded or open), via the radiopaque markers using a fluoroscopic or other image technique.

The medical practitioner may coupling a distal end of the implant tool to a coupling member of the shield (604). For example, the medical practitioner may couple tool distal end 406 to a coupling member of shield 31 or grab shield 31 with tool distal end 506. In some examples, as illustrated by FIG. 3E, a medical practitioner or assistant may fold or wrap shield 31 at least partially around a portion of implant tool 400 and couple a coupling member of shield 31 to implant tool 400 (or grip/grab shield 31 with distal end 606 of implant tool 600).

The medical practitioner may position, via the implant tool, the shield at the implant location (606), and the medical practitioner may deploy the shield between the implantable medical lead and tissue at the implant location anterior at least one of the electrodes of the implantable medical lead, e.g., at least one of a first defibrillation electrode, a second defibrillation electrode, or a pace electrode (608). In some examples, the medical practitioner may position and orient the shield using an implant tool 400 and/or 500 via one or more radiopaque markers. For example, shield 31 may include radiopaque markers 316, 326 and/or 336 and/or radiopaque components such as perimeter structure 314. The medical practitioner may identify the location, position, orientation (e.g., flipped or not), and/or configuration (e.g., folded or open), via the radiopaque markers using a fluoroscopic or other image technique. The medical practitioner may, if necessary, rotationally orient one or both of distal portion 16 of lead 10 and shield 31 so that shield 31 is positioned anteriorly relative to any of electrodes 28 and/or 32 of distal portion 16. In some examples, the medical practitioner may attach shield 31 to implantable medical lead 10, e.g., via a coupling member and/or one or more slits and/or slots of shield 31. In some examples, the medical practitioner may position shield 31 in the pleural cavity of patient 12, e.g., bounded laterally by pleurae 39, posteriorly by pericardium 38, and anteriorly by the sternum 22, and positioned anterior to distal portion 16. In some examples, the medical practitioner may position shield 31 between the heart and one or both lungs of patient 12, e.g., between pericardium 38 and pleurae 39 of patient 12.

Figure 7:
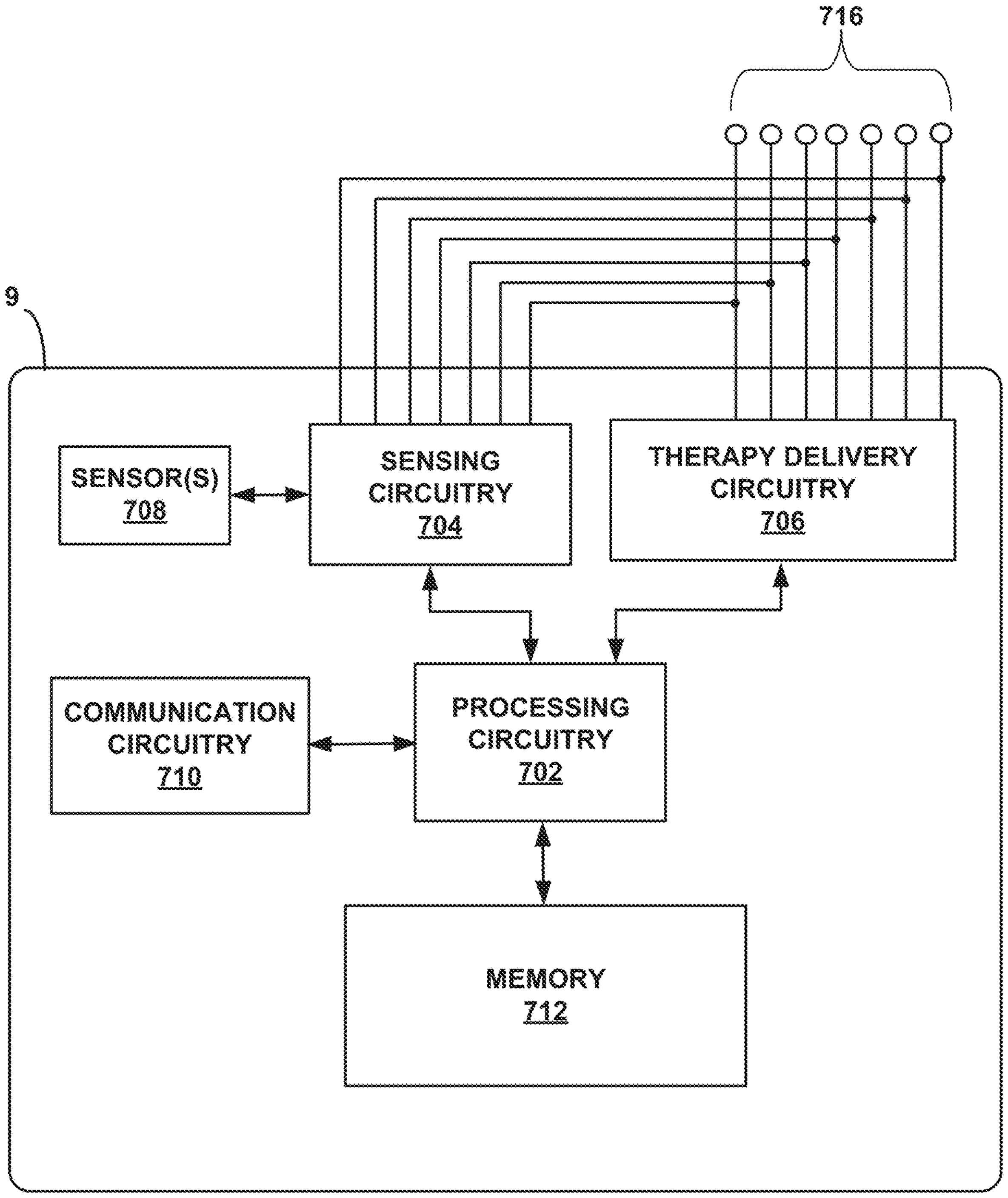
FIG. 7 is a functional block diagram of an example configuration of electronic components of an example ICD.

FIG. 7 is a functional block diagram of an example configuration of electronic components and other components of ICD 9. ICD 9 includes a processing circuitry 702, sensing circuitry 704, therapy delivery circuitry 706, sensors 708, communication circuitry 710, and memory 712. In other examples, ICD 9 may include more or fewer components. The described circuitry and other components may be implemented together on a common hardware component or separately as discrete but interoperable hardware or software components. Depiction of different features is intended to highlight different functional aspects and does not necessarily imply that such circuitry and other components must be realized by separate hardware or software components. Rather, functionality associated with one or more circuitries and components may be performed by separate hardware or software components, or integrated within common or separate hardware or software components.

Sensing circuitry 704 may be electrically coupled to some or all of electrodes 716, which may correspond to any of the defibrillation, pace/sense, and housing electrodes described herein. Sensing circuitry 704 is configured to obtain signals sensed via one or more combinations of electrodes 716 and process the obtained signals.

The components of sensing circuitry 704 may be analog components, digital components or a combination thereof. Sensing circuitry 704 may, for example, include one or more sense amplifiers, filters, rectifiers, threshold detectors, analog-to-digital converters (ADCs) or the like. Sensing circuitry 704 may convert the sensed signals to digital form and provide the digital signals to processing circuitry 702 for processing or analysis. For example, sensing circuitry 704 may amplify signals from the sensing electrodes and convert the amplified signals to multi-bit digital signals by an ADC. Sensing circuitry 704 may also compare processed signals to a threshold to detect the existence of atrial or ventricular depolarizations (e.g., P- or R waves) and indicate the existence of the atrial depolarization (e.g., P-waves) or ventricular depolarizations (e.g., R-waves) to processing circuitry 702. As shown in FIG. 7, ICD 9 may additionally include one or more sensors 708, such as one or more accelerometers, which may be configured to provide signals indicative of other parameters of a patient, such as activity or posture, to processing circuitry 702.

Processing circuitry 702 may process the signals from sensing circuitry 704 to monitor electrical activity of heart 26 of patient 12. Processing circuitry 702 may store signals obtained by sensing circuitry 704 as well as any generated EGM waveforms, marker channel data or other data derived based on the sensed signals in memory 712. Processing circuitry 702 may analyze the EGM waveforms and/or marker channel data to detect arrhythmias (e.g., bradycardia or tachycardia). In response to detecting the cardiac event, processing circuitry 702 may control therapy delivery circuitry 706 to deliver the desired therapy to treat the cardiac event, e.g., defibrillation shock, cardioversion shock, ATP, post shock pacing, or bradycardia pacing.

Therapy delivery circuitry 706 is configured to generate and deliver electrical therapy to heart 26. Therapy delivery circuitry 706 may include one or more pulse generators, capacitors, and/or other components capable of generating and/or storing energy to deliver as pacing therapy, defibrillation therapy, cardioversion therapy, cardiac resynchronization therapy, other therapy or a combination of therapies. In some instances, therapy delivery circuitry 706 may include a first set of components configured to provide pacing therapy and a second set of components configured to provide defibrillation therapy. In other instances, therapy delivery circuitry 706 may utilize the same set of components to provide both pacing and defibrillation therapy. In still other instances, therapy delivery circuitry 706 may share some of the defibrillation and pacing therapy components while using other components solely for defibrillation or pacing. Processing circuitry 702 may control therapy delivery circuitry 706 to deliver the generated therapy to heart 26 via one or more combinations of electrodes 716. Although not shown in FIG. 7, ICD 9 may include switching circuitry configurable by processing circuitry 702 to control which of electrodes 716 is connected to therapy delivery circuitry 706 and sensing circuitry 704.

Communication circuitry 710 includes any suitable hardware, firmware, software or any combination thereof for communicating with another device, such as a clinician programmer, a patient monitoring device, or the like. For example, communication circuitry 710 may include appropriate modulation, demodulation, frequency conversion, filtering, and amplifier components for transmission and reception of data with the aid of an antenna.

The various components of ICD 9 may include any one or more processors, controllers, digital signal processors (DSPs), application specific integrated circuits (ASICs), field-programmable gate arrays (FPGAs), or equivalent discrete or integrated circuitry, including analog circuitry, digital circuitry, or logic circuitry. Processing circuitry 702 may include fixed function circuitry and/or programmable processing circuitry. The functions attributed to processing circuitry 702 herein may be embodied as software, firmware, hardware or any combination thereof.

Memory 712 may include computer-readable instructions that, when executed by processing circuitry 702 or other components of ICD 9, cause one or more components of ICD 9 to perform various functions attributed to those components in this disclosure. Memory 712 may include any volatile, non-volatile, magnetic, optical, or electrical media, such as a random-access memory (RAM), read-only memory (ROM), non-volatile RAM (NVRAM), static non-volatile RAM (SRAM), electrically-erasable programmable ROM (EEPROM), flash memory, or any other non-transitory computer-readable storage media.

The leads and systems described herein may be used at least partially within the substernal space, e.g., within anterior mediastinum of patient, to provide an extravascular ICD system. An implanter (e.g., physician) may implant the distal portion of the lead intra-thoracically using any of a number of implant tools, e.g., tunneling rod, sheath, or other tool that can traverse the diagrammatic attachments and form a tunnel in the substernal location. For example, the implanter may create an incision near the center of the torso of the patient, e.g., and introduce the implant tool into the substernal location via the incision. The implant tool is advanced from the incision superior along the posterior of the sternum in the substernal location. The distal portion of the lead is introduced into the tunnel via implant tool (e.g., via a sheath). As the distal portion is advanced through the substernal tunnel, the distal portion is relatively straight. The pre-formed or shaped undulating configuration is flexible enough to be straightened out while routing the lead through a sheath or other lumen or channel of the implant tool. Once the distal portion is in place, the implant tool is withdrawn toward the incision and removed from the body of the patient while leaving the lead in place along the substernal path. As the implant tool is withdrawn, the distal end of the lead takes on its pre-formed undulating configuration, and the shield transitions to its deployed configuration.

In some examples, rather than extending in a superior direction along the sternum, the distal portion of the lead may be oriented orthogonal or otherwise transverse to the sternum and/or inferior to the heart. In such examples, the lead may include one or more shields that cover a portion of an outer surface of one or more electrodes, e.g., an anterior and/or inferior portion, according to any of the examples described herein. Such shield(s) may impede an electrical field in a direction away from the heart, which may be an anterior and/or inferior direction.

In this way, various aspects of the techniques may enable the following examples.

Example 1: A medical device system including: an implantable medical lead including: a first defibrillation electrode and a second defibrillation electrode, the first and second defibrillation electrodes configured to deliver anti-tachyarrhythmia shocks; and a pace electrode disposed between the first defibrillation electrode and the second defibrillation electrode, the pace electrode configured to deliver a pacing pulse that generates an electric field proximate to the pace electrode; and a shield configured to be implanted in a patient separately from the implantable medical lead and disposed anterior at least one of the electrodes, wherein the shield is configured to impede an electric field of the electrical therapy in a direction from at least one of the first defibrillation electrode, the second defibrillation electrode, or the pace electrode away from a heart of the patient.

Example 2: The medical device system of example 1, the shield further comprising one or more radiopaque markers.

Example 3: The medical device system of example 2, wherein the one or more radiopaque markers comprise an edge marker extending along an outer perimeter of the shield.

Example 4: The medical device system of examples 2 or example 3, wherein the one or more radiopaque markers comprise markers configured to indicate at least one of an orientation or a position of the shield.

Example 5: The medical device system of example 4, wherein the one or more radiopaque markers comprise triangular shaped markers.

Example 6: The medical device system of any one of examples 1 through 5, wherein the shield is elastic.

Example 7: The medical device system of any one of examples 1 through 6, wherein the shield further comprises a guide configured to couple to the implantable medical lead while the shield is implanted.

Example 8: The medical device system of any one of examples 1 through 7, wherein the shield is configured to attach to the implantable medical lead when the shield is implanted.

Example 9: The medical device assembly of any one of examples 1 through 8, wherein the shield comprises at least one slit.

Example 10: The medical device system of any one of examples 1 through 9, wherein the implantable medical lead is implanted within an anterior mediastinum of a patient.

Example 11: The medical device system of any one of examples 1 through 10, further comprising a tool extending to a tool distal end, the tool distal end configured to couple with the shield, the tool configured to implant the shield when the tool distal end is coupled with the shield.

Example 12: The medical device system of example 11, wherein the shield further comprises a coupling member configured to couple with the tool distal end.

Example 13: The medical device system of example 11 or example 12, wherein the tool distal end includes a hook.

Example 14: The medical device system of any one of examples 11 through 13, wherein the tool is configured to attach the shield to the implantable medical lead when the implantable medical lead is implanted within the patient.

Example 15: The medical device system of any one of examples 11 through 14, wherein the tool is configured to at least one of position or orient the shield relative to the implantable medical lead when the implantable medical lead is implanted within the patient.

Example 16: The medical device system of example 15, wherein the tool is configured to at least one of position or orient the shield by releasing the shield from a wrapped or folded configuration to an open configuration.

Example 17: The medical device system of any one of examples 1 through 16, wherein a length of the shield is greater than a length first defibrillation electrode, the pace electrode, and the second defibrillation electrode of the implantable medical lead.

Example 18: The medical device system of any one of examples 1 through 17, wherein the shield extends laterally away from at least one of the first defibrillation electrode, the second defibrillation electrode, or the pace electrode.

Example 19: The medical device system of example any one of examples 1 through 18, wherein a distal portion of the implantable medical lead defines an undulating configuration including a first peak extending in a first direction, a second peak extending in the first direction, and a third peak, between the first peak and the second peak, extending in a second direction opposite the first direction, and wherein at least a portion of the first defibrillation electrode is disposed on the first peak, at least a portion of the second defibrillation electrode is disposed on the second peak, and at least a portion of the pace electrode is disposed on the third peak.

Example 20: The medical device system of example 19, wherein the shield extends laterally away from the implantable medical lead.

Example 21: The medical device system of any one of examples 1 through 20, wherein the shield is electrically insulative.

Example 22: The medical device system of any one of examples 1 through 21, wherein the shield is configured to impede an electric field of the electrical therapy in a direction from at least one of the first defibrillation electrode, the second defibrillation electrode, or the pace electrode away from a heart of the patient and near an edge of at least one of the first defibrillation electrode, the second defibrillation electrode, or the pace electrode.

Example 23: A method including: positioning an implantable medical lead at an implant location within a patient, wherein the implantable medical lead comprises: a first defibrillation electrode and a second defibrillation electrode, the first and second defibrillation electrodes configured to deliver antitachyarrhythmia shocks; a pace electrode disposed between the first defibrillation electrode and the second defibrillation electrode, the pace electrode configured to deliver a pacing pulse that generates an electric field proximate to the pace electrode; coupling a distal end of a tool to a coupling member of a shield, wherein the shield is configured to impede an electric field of the electrical therapy in a direction from at least one of the first defibrillation electrode, the second defibrillation electrode, or the pace electrode away from a heart of the patient; positioning, via the tool, the shield at the implant location; and deploying the shield between the implantable medical lead and tissue at the implant location anterior at least one of the first defibrillation electrode, the second defibrillation electrode, or the pace electrode, wherein, when deployed, the shield is configured to impede an electric field in a direction from the at least one electrode away from the heart.

Example 24: The method of example 23, wherein the shield comprises one or more radiopaque markers, the method further comprising positioning the shield, via the tool, using the one or more radiopaque markers.

Example 25: The method of example 23 or example 24 or any of examples 23 and 24, wherein the shield is elastic.

Example 26: The method of any one of examples 23 through 25, wherein the shield further comprises a guide slot configured to couple to the implantable medical lead while the shield is positioned.

Example 27: The method of any one of examples 23 through 26, further comprising attaching the shield to the implantable medical lead.

Example 28: The method of any one of examples 23 through 27, wherein the shield comprises at least one slit.

Example 29: The method of any one of examples 23 through 28, wherein the implant location is an anterior mediastinum of a patient.

Example 30: The method of any one of examples 23 through 29, wherein the distal end of the tool includes a hook.

Example 31: The method of any one of examples 23 through 30, wherein deploying the shield comprises releasing the shield from a wrapped or folded configuration to an open configuration.

Example 32: The method of any one of examples 23 through 31, wherein a length of the shield is greater than a length of the implantable medical lead.

Example 33: The method of any one of examples 23 through 32, wherein the shield extends laterally away from at least one of the first defibrillation electrode, the second defibrillation electrode, or the pace electrode.

Example 34: The method of any one of examples 23 through 33, wherein a distal portion of the implantable medical lead defines an undulating configuration including a first peak extending in a first direction, a second peak extending in the first direction, and a third peak, between the first peak and the second peak, extending in a second direction opposite the first direction, and wherein at least a portion of the first defibrillation electrode is disposed on the first peak, at least a portion of the second defibrillation electrode is disposed on the second peak, and at least a portion of the pace electrode is disposed on the third peak.

Example 35: The method of any one of examples 23 through 34, wherein the shield extends laterally away from the implantable medical lead.

Example 36: The method of any one of examples 23 through 35, wherein the shield is electrically insulative.

Example 37: A shield including: a biocompatible material configured to be configured to be implanted in a patient separately from an implantable medical lead and disposed anterior at least one electrode of the implantable medical lead, wherein the shield is configured to impede an electric field of the at least one electrode in a direction from the at least one electrode away from a heart of the patient; and one or more radiopaque markers configured to indicate at least one of an orientation or a position of the shield.

It will be appreciated by persons skilled in the art that the present application is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the application, which is limited only by the following claims.

What is claimed is:

1. A medical device system comprising:

an implantable medical lead comprising:

a first defibrillation electrode and a second defibrillation electrode, the first and second defibrillation electrodes configured to deliver anti-tachyarrhythmia shocks; and a pace electrode disposed between the first defibrillation electrode and the second defibrillation electrode, the pace electrode configured to deliver a pacing pulse that generates an electric field proximate to the pace electrode; and a shield configured to be implanted in a patient separately from the implantable medical lead and disposed anterior at least one of the electrodes, wherein the shield is configured to impede an electric field of an electrical therapy in a direction from at least one of the first defibrillation electrode, the second defibrillation electrode, or the pace electrode away from a heart of the patient, wherein the shield comprises a coupling member configured to attach to the implantable medical lead when the shield is implanted.

2. The medical device system of claim 1, the shield further comprising one or more radiopaque markers, wherein the one or more radiopaque markers comprise an edge marker extending along an outer perimeter of the shield, wherein the one or more radiopaque markers comprise markers configured to indicate at least one of an orientation or a position of the shield, wherein the one or more radiopaque markers comprise triangular shaped markers, and wherein the shield is elastic.

3. The medical device system of claim 1, wherein the shield further comprises a guide configured to couple to the implantable medical lead while the shield is implanted.

4. The medical device system of claim 1, wherein the shield comprises at least one slit.

5. The medical device system of claim 1, further comprising a tool extending to a tool distal end, the tool distal end configured to couple with the shield, the tool configured to implant the shield when the tool distal end is coupled with the shield.

6. The medical device system of claim 5, wherein the shield further comprises a coupling member configured to couple with the tool distal end, wherein the tool distal end includes a hook, wherein the tool is configured to attach the shield to the implantable medical lead when the implantable medical lead is implanted within the patient, wherein the tool is configured to at least one of position or orient the shield relative to the implantable medical lead when the implantable medical lead is implanted within the patient, and wherein the tool is configured to at least one of position or orient the shield by releasing the shield from a wrapped or folded configuration to an open configuration.

7. The medical device system of claim 1, wherein a length of the shield is greater than a length of the first defibrillation electrode, the pace electrode, and the second defibrillation electrode of the implantable medical lead, and wherein the shield extends laterally away from at least one of the first defibrillation electrode, the second defibrillation electrode, or the pace electrode.

8. The medical device system of claim 1, wherein a distal portion of the implantable medical lead defines an undulating configuration including a first peak extending in a first direction, a second peak extending in the first direction, and a third peak, between the first peak and the second peak, extending in a second direction opposite the first direction, and wherein at least a portion of the first defibrillation electrode is disposed on the first peak, at least a portion of the second defibrillation electrode is disposed on the second peak, and at least a portion of the pace electrode is disposed on the third peak.

9. The medical device system of claim 1, wherein the shield is electrically insulative.

10. The medical device system of claim 1, wherein the shield is configured to be positioned anterior to the pace electrode and at least a portion of at least one of the defibrillation electrodes, and to suppress an edge effect of delivery of an antitachyarrhythmia shock via the at least one of the defibrillation electrodes.

11. A method comprising:

positioning an implantable medical lead at an implant location within a patient, wherein the implantable medical lead comprises:

a first defibrillation electrode and a second defibrillation electrode, the first and second defibrillation electrodes configured to deliver anti-tachyarrhythmia shocks;

a pace electrode disposed between the first defibrillation electrode and the second defibrillation electrode, the pace electrode configured to deliver a pacing pulse that generates an electric field proximate to the pace electrode;

coupling a distal end of a tool to a coupling member of a shield, wherein the shield is configured to impede an electric field of an electrical therapy in a direction from at least one of the first defibrillation electrode, the second defibrillation electrode, or the pace electrode away from a heart of the patient;

positioning, via the tool, the shield at the implant location; and deploying the shield between the implantable medical lead and tissue at the implant location anterior at least one of the first defibrillation electrode, the second defibrillation electrode, or the pace electrode, wherein, when deployed, the shield is configured to impede an electric field in a direction from the at least one of the first defibrillation electrode, the second defibrillation electrode, or the pace electrode away from the heart.

12. The method of claim 11, wherein the shield comprises one or more radiopaque markers, the method further comprising positioning the shield, via the tool, using the one or more radiopaque markers.

13. The method of claim 11, wherein the shield further comprises a guide slot configured to couple to the implantable medical lead while the shield is positioned.

14. The method of claim 11, further comprising attaching the shield to the implantable medical lead.

15. The method of claim 11, wherein the implant location is an anterior mediastinum of a patient.

16. The method of claim 11, wherein the distal end of the tool includes a hook.

17. The method of claim 11, wherein deploying the shield comprises releasing the shield from a wrapped or folded configuration to an open configuration.

18. The method of claim 11, wherein positioning the shield comprises positioning the shield anterior to the pace electrode and at least a portion of at least one of the first defibrillation electrode or the second defibrillation electrode to suppress an edge effect of delivery of an antitachyarrhythmia shock via the at least one first defibrillation electrode or second defibrillation electrode.

19. A shield comprising:

a biocompatible material configured to be implanted in a patient separately from an implantable medical lead and disposed anterior at least one electrode of the implantable medical lead, wherein the shield is configured to impede an electric field of the at least one electrode in a direction from the at least one electrode away from a heart of the patient;

one or more radiopaque markers configured to indicate at least one of an orientation or a position of the shield; and a first coupling member configured to attach to a distal end of a tool when the shield is implanted.

* * * * *